(12) United States Patent
Sivik

(10) Patent No.: US 6,395,695 B1
(45) Date of Patent: May 28, 2002

(54) PRO-FRAGRANCE LINEAR ACETALS AND KETALS

(75) Inventor: Mark Robert Sivik, Fairfield, OH (US)

(73) Assignee: The Procter & Gamble Company, Cinncinnati, OH (US)

(*) Notice: Subject to any disclaimer, the term of this patent is extended or adjusted under 35 U.S.C. 154(b) by 0 days.

(21) Appl. No.: 09/917,542

(22) Filed: Jul. 27, 2001

Related U.S. Application Data

(63) Continuation of application No. 09/445,325, filed as application No. PCT/US98/13281 on Jun. 26, 1998, now Pat. No. 6,316,397.
(60) Provisional application No. 60/051,104, filed on Jun. 27, 1997.

(51) Int. Cl.[7] .......................... C11D 14/02; D06L 14/02
(52) U.S. Cl. ....................... 510/276; 510/276; 510/101; 568/579
(58) Field of Search ................................ 510/101, 276; 568/579

(56) References Cited

U.S. PATENT DOCUMENTS

| | | |
|---|---|---|
| 3,779,932 A | 12/1973 | Jaggers et al. |
| 3,849,326 A | 11/1974 | Jaggers et al. |
| 4,524,018 A | 6/1985 | Yemoto et al. |
| 4,994,266 A | 2/1991 | Wells |
| 5,081,111 A | 1/1992 | Akimoto et al. |
| 5,232,612 A | 8/1993 | Trinh et al. |
| 5,266,592 A | 11/1993 | Grub et al. |
| 5,378,468 A | 1/1995 | Suffis et al. |
| 5,500,138 A * | 3/1996 | Bacon et al. ................. 252/8.8 |
| 5,506,201 A | 4/1996 | McDermott et al. |
| 5,739,100 A | 4/1998 | Horino et al. |
| 5,968,893 A * | 10/1999 | Manohar et al. ............ 510/475 |

FOREIGN PATENT DOCUMENTS

| | | | |
|---|---|---|---|
| DE | 2132898 | * | 1/1973 |
| EP | 786247 A1 | | 7/1997 |
| JP | 05-230496 | | 9/1993 |
| WO | WO 95/04809 | | 2/1995 |

OTHER PUBLICATIONS

P.M. Muller, D. Lamparsky, *Perfumes Art, Science & Technology*, Blackie Academic & Professional, NY, 1994, Chapters 1,6, and 7.

* cited by examiner

*Primary Examiner*—Mark Kopec
*Assistant Examiner*—Eisa Elhilo
(74) *Attorney, Agent, or Firm*—Richard S. Echler, Sr.; C. Brant Cook; Kim W. Zerby

(57) ABSTRACT

The present invention relates to a fragrance delivery system for use in laundry detergent compositions including rinse-added and dryer-added fabric conditioning compositions which provides a long lasting "freshness" or "clean" scent to fabric. The compositions described herein deliver highly fabric substantive linear acetal and/or ketal pro-fragrances to the fabric surface during laundering wherein the pro-fragrances release their fragrance raw materials over a period of up to two weeks. The present invention also relates a method for delivering a pleasurable scent to fabric which has a lasting freshness quality by contacting the fabric with a laundry detergent composition which comprises the fragrance-releasable pro-fragrances.

27 Claims, No Drawings

PRO-FRAGRANCE LINEAR ACETALS AND KETALS

CROSS-REFERENCE

This application is a continuation to application Ser. No. 09/445,325, filed in the USPTO on Jul. 7, 2000; now U.S. Pat. No. 6,316,397 which is 371 of application PCT/US98/13281 filed in the PCT on Jun. 26, 1998; and application Ser. No. 60/051,104 filed in the USPTO on Jun. 27, 1997.

FIELD OF THE INVENTION

The present invention relates to pro-fragrance compounds useful in laundry detergent compositions. The pro-fragrance compounds comprise a fragrance raw material component and a solubility or substantivity component which can be independently adjusted to meet the specific requirements of the formulator. The pro-fragrance compounds are especially useful for delivering a "through the wash" fresh-like or clean-like fragrance to fabric which remains on the fabric and is continuously released for extended periods after the conclusion of the laundry cycle.

BACKGROUND OF THE INVENTION

In addition to the removal of stains, dirt, soil, grime, and grease from fabric, laundry detergent formulators have attempted to deliver a "fresh" or "clean" odor to washed clothing to provide an olfactory aesthetic benefit and to serve as a signal that the product is effective. Laundry detergent compositions, including rinse-added fabric softeners and dryer-added substrates, are currently formulated with perfume and fragrance ingredients which are aesthetically pleasing to the consumer but which fail to deliver a prolonged "fragrance" or "pleasurable smell" to the finished, cleaned fabric.

Among the most readily perceived fragrance materials are the perfume "top" and "middle" notes which are highly volatile compounds and which are usually detectable at low levels. However, these highly volatile materials are typically lost either during the prolonged heating which takes place in an automatic dryer or they lack the substantivity necessary to deposit onto the fabric surface and are therefore lost during the laundry rinsing process.

Attempts have been made to deliver perfume ingredients onto fabric which can survive the laundry rinsing and drying cycles and therefore provide a residual "fresh" or "clean" odor to the washed material. However, none of these attempts have suitably provided fabric with a protracted release of fragrance raw materials which provide a "fresh" or "clean" smell for a period up to two weeks after washing. There has especially been a long felt need to deliver certain tertiary alcohol fragrance raw materials inter alia linalool and dihydromyrcenol.

Accordingly, there remains a need in the art for a fragrance delivery system wherein perfume raw materials are delivered to fabric by way of a laundry detergent composition which provides the cleaned clothing or fabric with a "fresh" or "clean" smell for a period up to two weeks after washing. Also, there is a need for fragrance releasing compounds which deliver a "fresh" or "clean" fragrance in which the solubility and substantivity properties of the compound can be varied to match various formulation and delivery parameters inter alia compatibility with surface active adjuncts and fabric type. In addition, there is a need for a fragrance delivery system suitable for providing sustained release or enhanced longevity fragrances to a variety of personal care and personal hygiene products inter alia deodorants, body lotions or creams, and shampoos.

BACKGROUND ART

The following relate to the subject matter of fragrance ingredients. U.S. Pat. No. 5,232,612 Trinh et al., issued Aug. 3, 1996; U.S. Pat. No. 5,506,201 McDermott et al., issued Apr. 9, 1996; U.S. Pat. No. 5,378,468 Suffis et al., issued Jan. 3, 1995; U.S. Pat. No. 5,266,592 Grub et al., issued Nov. 30, 1993; U.S. Pat. No. 5,081,111 Akimoto et al., issued Jan. 14, 1992; U.S. Pat. No. 4,994,266 Wells, issued Feb. 19, 1991; U.S. Pat. No. 4,524,018 Yemoto et al., issued Jun. 18, 1985; U.S. Pat. No. 3,849,326 Jaggers et al., issued Nov. 19, 1974; U.S. Pat. No. 3,779,932 Jaggers et al., issued Dec. 18, 1973; JP 07-179,328 published Jul. 18, 1995; JP 05-230496 published Sep. 7, 1993; WO 96/14827 published May 23, 1996; WO 95/04,809 published Feb. 16, 1995; and WO 95/16660 published Jun. 22, 1995. In addition, P. M. Muller, D. Lamparsky *Perfumes Art, Science*, & *Technology* Blackie Academic & Professional, (New York, 1994) is included herein by reference.

SUMMARY OF THE INVENTION

The present invention meets the aforementioned needs in that it has been surprisingly discovered that certain linear acetals and ketals can be used to deliver perfume or fragrance raw materials onto fabric "through the wash" from a single precursor pro-fragrance molecule having variable fabric substantivity, variable solubility as well as variable fragrance release rate. These pro-fragrances can be used to deliver tertiary alcohol raw materials as well as primary and secondary fragrance raw material alcohols which impart a "fresh" or "clean" aesthetic odor benefit to fabric or to human skin when the skin is contacted with a personal care or personal hygiene product inter alia deodorants, body lotions or creams, and shampoos, which comprises the pro-fragrances of the present invention In addition to the short-term pleasurable odor benefits, the pro-fragrances according to the present invention continue to release their fragrance raw materials for as long as several weeks depending upon the structure of the pro-accord.

The pro-fragrances described herein comprise fragrance raw materials in a stable, releasable form. The pro-fragrance containing laundry detergent compositions of the present invention can comprise any number of pro-fragrances and are suitable for delivery of any type of fragrance "characteristic" desired by the formulator.

The first aspect of the present invention relates to pro-fragrance compounds having the formula:

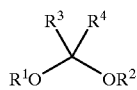

$R^1$ and $R^2$ are each independently:
a) $C_8$–$C_{22}$, preferably $C_8$–$C_{12}$ linear or branched alkyl;
b) $C_8$–$C_{22}$, preferably $C_8$–$C_{12}$ linear or branched alkenyl;
c) $C_2$–$C_{20}$, preferably $C_2$–$C_{12}$, more preferably $C_2$–$C_6$ substituted or unsubstituted alkyleneoxy;
d) $C_3$–$C_{20}$, preferably $C_3$–$C_{12}$, more preferably $C_3$–$C_6$ substituted or unsubstituted alkyleneoxyalkyl;
e) $C_7$–$C_{20}$, preferably $C_7$–$C_{12}$, more preferably $C_7$ substituted or unsubstituted alkylenearyl;
f) $C_6$–$C_{20}$, preferably $C_6$–$C_{10}$, more preferably $C_6$ substituted or unsubstituted aryloxy;

g) $C_7$–$C_{20}$, preferably $C_8$–$C_{12}$, more preferably $C_8$ substituted or unsubstituted alkyleneoxyaryl;

h) $C_7$–$C_{20}$, preferably $C_7$–$C_{11}$, more preferably $C_7$ oxyalkylenearyl;

i) $C_2$–$C_{20}$, preferably $C_2$–$C_{12}$, more preferably $C_2$–$C_6$ alkylenecarboxy having the formula:

—$(CH_2)_x R^9$ wherein $R^9$ is —CHO, —$CO_2M$; —$CO_2R^{10}$, —$CONH_2$, —$CONHR^{10}$, $CONR^{10}R^{11}$, and mixtures thereof; wherein $R^{10}$ and $R^{11}$ are each independently $C_1$–$C_{12}$ linear or branched alkyl, preferably methyl or ethyl; M is hydrogen or a salt forming cation, preferably sodium or potassium; x is an integer from 1 to 19;

j) an anionic unit having the formula:

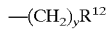

—$(CH_2)_y R^{12}$ wherein $R^{12}$ is —$SO_3M$, —$OSO_3M$, —$PO_3M$, —$OPO_3M$, or mixtures thereof;

wherein M is hydrogen, one or more salt forming cations sufficient to satisfy charge balance, preferably sodium or potassium; or mixtures thereof; y is an interger from 1 to about 22;

k) and mixtures thereof;

$R^3$ and $R^4$ are each independently hydrogen, methyl, ethyl, propyl, phenyl, benzyl, and mixtures thereof.

The present invention also relates to laundry detergent compositions which comprise the pro-fragrance linear acetals and ketals described herein. A further aspect of the present invention is the use of the linear acetal and ketal pro-fragrances of the present invention as a post-laundry "freshening agent" for use on fabric which has been laundered but which has not been worn for an extended period of time. A yet further aspect of the present invention is the use of the pro-fragrances of the present invention in rinse-added compositions and in dryer-added compositions. These and other objects, features and advantages will become apparent to those of ordinary skill in the art from a reading of the following detailed description and the appended claims.

All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The pro-fragrances of the present invention comprise a fragrance raw material component and a substantivity or solubility component. The fragrance raw material component can be any perfume or any "fragrance raw material alcohol" which the formulator wishes to deliver to the fabric surface for subsequent release after the laundry cycle. In addition, the pro-fragrances comprise a substantivity or solubility component wherein the proper choice of group allows the formulator to control the solubility of the pro-fragrance in water, the degree of substantivity of the pro-fragrance for fabric, or the bulk properties of the material. The manipulation of the pro-fragrance bulk properties will allow the formulator to produce a pro-fragrance which is more easily admixed into a particular type of laundry detergent, for example, liquid, granular, high density, encapsulated-component, etc.

Once the laundry process is complete and the pro-fragrance has been suitably delivered to the fabric, the pro-fragrance begins to release the fragrance raw material and because this release of material is protracted, the fabric remains "fresh" and "clean" smelling longer. However, pro-fragrances according to the present invention can also be designed to be activated by a change in pH or to be moisture or "heat activated" so as to release a "freshening scent" to the fabric during drying. Therefore, heat-activated pro-fragrances can be delivered to the fabric surface. This results in a fabric having high "initial scent" as well as the lower "clean" and "fresh" scent obtained by the protracted release of non-activated pro-fragrances What is meant herein by "heat activated" pro-fragrances are compounds which have a higher release rate of their fragrance materials after exposure to elevated temperatures. Therefore the formulator may achieve an initial high fragrance delivery coupled with the longer term sustained release.

The pro-fragrances of the present invention are therefore a means for delivering a desired fragrance raw material onto fabric and thereby providing the fabric with a longer and more sustained "fresh" or "clean" smell. For the purposes of the present invention the term "fragrance raw material alcohol" is defined as "an alcohol generally having a molecular weight greater than or equal to 100 g/mol which provides a fragrance, scent, smell, odor, or character which is generally deemed pleasurable to the senses."

Most of the fragrance raw materials which comprise the pro-fragrances of the present invention are not deliverable as individual compounds to fabric via the laundry cycle either due to solubility factors (lost or rinsed away during the laundry cycles), substantivity factors (do not sufficiently adhere to fabric surface), or volatility factors (evaporation during the drying cycle). Therefore, the pro-fragrances described herein are a means for delivering certain fragrance raw materials to fabric which could not have previously been effectively or efficiently delivered. In fact, the tertiary alcohol fragrance raw materials are more suitably delivered by the pro-fragrances of the present invention than by conventional pro-fragrances.

The "fragrance raw materials" which comprise the preferred embodiments are fragrance raw material alcohols. A listing of common fragrance raw material alcohols can be found in various reference sources, for example, "Perfume and Flavor Chemicals", Vols. I and II; Steffen Arctander Allured Pub. Co. (1994) and "Perfumes: Art, Science and Technology"; Müller, P. M. and Lamparsky, D., Blackie Academic and Professional (1994) all of which are incorporated herein by reference.

Those skilled in the art of detergent compositions will recognize that the terms "substantive" and "substantivity" refer to the propensity of a compound to adhere to, associate with, or deposit upon a surface, preferably the surface of fabric. Therefore, compounds which are more substantive more readily adhere to fabric surface. However, substantive compounds, in general, do not react with the surface onto which they deposit.

Pro-fragrances

The pro-fragrances of the present invention are derivatives of aldehydes and ketones having the formula:

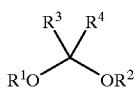

$R^1$ and $R^2$ are each independently:
  a) $C_8$–$C_{22}$, preferably $C_8$–$C_{12}$ linear or branched alkyl;
  b) $C_8$–$C_{22}$, preferably $C_8$–$C_{12}$ linear or branched alkenyl;
  c) $C_2$–$C_{20}$, preferably $C_2$–$C_{12}$, more preferably $C_2$–$C_6$ substituted or unsubstituted alkyleneoxy;
  d) $C_3$–$C_{20}$, preferably $C_3$–$C_{12}$, more preferably $C_3$–$C_6$ substituted or unsubstituted alkyleneoxyalkyl;
  e) $C_7$–$C_{20}$, preferably $C_7$–$C_{12}$, more preferably $C_7$ substituted or unsubstituted alkylenearyl;
  f) $C_6$–$C_{20}$, preferably $C_6$–$C_{10}$, more preferably $C_6$ substituted or unsubstituted aryloxy;
  g) $C_7$–$C_{20}$, preferably $C_8$–$C_{12}$, more preferably $C_8$ substituted or unsubstituted alkyleneoxyaryl;
  h) $C_7$–$C_{20}$, preferably $C_7$–$C_{11}$, more preferably $C_7$ oxyalkylenearyl;
  i) $C_2$–$C_{20}$, preferably $C_2$–$C_{12}$, more preferably $C_2$–$C_6$ alkylenecarboxy having the formula:

—(CH$_2$)$_x$R$^9$ wherein $R^9$ is —CHO, —CO$_2$M; —CO$_2$R$^{10}$, —CONH$_2$, —CONHR$^{10}$, CONR$^{10}$R$^{11}$, and mixtures thereof; wherein $R^{10}$ and $R^{11}$ are each independently $C_1$–$C_{12}$ linear or branched alkyl, preferably methyl or ethyl; M is hydrogen or a salt forming cation, preferably sodium or potassium; x is an integer from 1 to 19;
  j) an anionic unit having the formula:

—(CH$_2$)$_y$R$^{12}$ wherein $R^{12}$ is —SO$_3$M, —OSO$_3$M, —PO$_3$M, —OPO$_3$M, or mixtures thereof;
  wherein M is hydrogen, one or more salt forming cations sufficient to satisfy charge balance, preferably sodium or potassium; or mixtures thereof; y is an interger from 1 to about 22;
  k) and mixtures thereof;
$R^3$ and $R^4$ are each independently hydrogen, methyl, ethyl, propyl, phenyl, benzyl, and mixtures thereof.

More preferably $R^1$ and $R^2$ are 2,4-dimethyl-3-cyclohexene-1-methyl (Floralol), 2,4-dimethyl cyclohexane methyl (Dihydro floralol), 5,6-dimethyl-1-methylethenylbicyclo[2.2.1]hept-5-ene-2-methyl (Arbozol), 2,4,6-trimethyl-3-cyclohexene-1-methyl (Isocyclo geranyl), 4-(1-methylethyl)cyclohexylmethyl (Mayol), a-3,3-trimethyl-2-norboranylmethyl, 1,1-dimethyl-1-(4-methylcyclohex-3-enyl)methyl, 2-phenylethyl, 2-cyclohexylethyl, 2-(o-methylphenyl)ethyl, 2-(m-methylphenyl)ethyl, 2-(p-methylphenyl)ethyl, 6,6-dimethylbicyclo[3.1.1]hept-2-ene-2-ethyl (nopyl), 2-(4-methylphenoxy)ethyl, 3,3-dimethyl-D$^2$-b-norbomanylethyl, 2-methyl-2-cyclohexylethyl, 1-(4-isopropylcyclohexyl) ethyl, 1-phenyl-1-hydroxyethyl, 1,1-dimethyl-2-phenylethyl, 1,1-dimethyl-2-(4-methylphenyl)ethyl, 1-phenylpropyl, 3-phenylpropyl, 2-phenylpropyl (Hydrotropic Alcohol), 2-(cyclododecyl)-propan-1-yl (Hydroxyambran), 2,2-dimethyl-3-(3-methylphenyl) propan-1-yl (Majantol), 2-methyl-3-phenylpropyl, 3-phenyl-2-propen-1-yl (cinnamyl alcohol), 2-methyl-3-phenyl-2-propen-1-yl (methylcinnamyl alcohol), a-n-pentyl-3-phenyl-2-propen-1-yl (a-amylcinnamyl alcohol), ethyl-3-hydroxy-3-phenylpropionate, 2-(4-methylphenyl)-2-propyl, 3-(4-methylcyclohex-3-ene)butyl, 2-methyl-4-(2, 2,3-trimethyl-3-cyclopenten-1-yl)butyl, 2-ethyl-4-(2,2,3-trimethylcyclopent-3-enyl)-2-buten-1-yl, 3-methyl-2-buten-1-yl, 2-methyl-4-(2,2,3-trimethyl-3-cyclopenten-1-yl)-2-buten-1-yl, 3-hydroxy-2-butanone, ethyl 3-hydroxybutyrate, 4-phenyl-3-buten-2-yl, 2-methyl-4-phenylbutan-2-yl, 4-(4-hydroxyphenyl)butan-2-one, 4-(4-hydroxy-3-methoxyphenyl)butan-2-one, cis-3-pentenyl, 3-methylpentyl, 3-methyl-3-penten-1-yl, 2-methyl-4-phenylpentyl (Pamplefleur), 3-methyl-5-phenylpentyl (Phenoxanyl), 2-methyl-5-phenylpentyl, 2-methyl-5-(2,3-dimethyltricyclo-[2.2.1.0(2,6)]hept-3-yl)-2-penten-1-yl (santalyl), 4-methyl-1-phenyl-2-pentyl, (1-methyl-bicyclo [2.1.1]hepten-2-yl)-2-methylpent-1-en-3-yl, 3-methyl-1-phenylpent-3-yl, 1,2-dimethyl-3-(1-methylethenyl) cyclopent-1-yl, 2-isopropyl-4-methyl-2-hexenyl, cis-3-hexen-1-yl, trans-2-hexen-1-yl, 2-isopropenyl-5-methyl-4-hexen-1-yl (Lavandulyl), 2-ethyl-2-prenyl-3-hexenyl (silwanol), 2-ethylhexyl, 1-hydroxymethyl-4-isopropenyl-1-cyclohexenyl (Dihydrocuminyl), 1-methyl-4-isopropenylcyclohex-6-en-2-yl (carvenyl), 6-methyl-3-isopropenylcyclohex-1-yl, 1-methyl-4-isopropenylcyclohex-3-yl, 4-iso-propyl-1-methylcyclohex-3-yl, 4-tert-butylcyclohexyl, 2-tert-butylcyclohexyl, 2-tert-butyl-4-methylcyclohexyl, 4-isopropylcyclohexyl, 4-methyl-1-(1-methylethyl)-3-cyclohexen-1-yl, 2-(5,6,6-trimethyl-2-norbornyl)cyclohexyl, isobornylcyclohexyl, 3,3,5-trimethylcyclohexyl, 1-methyl-4-isopropylcyclohex-3-yl (menthol), 1,2-dimethyl-3-(1-methylethyl)-cyclohexan-1-yl, heptyl, 2,4-dimethylhept-1-yl, 2,4-dimethyl-2,6-heptandienyl, 6,6-dimethyl-2-oxymethylbicyclo[3.1.1]hept-2-en-1-yl (myrtenyl), 4-methyl-2,4-heptadien-1-yl, 3,4,5,6, 6-pentamethyl-2-heptyl, 3,6-dimethyl-3-vinyl-5-hepten-2-yl, 6,6-dimethyl-3-hydroxy-2-methylenebicyclo[3.1.1]-heptyl, 1,7,7-trimethylbicyclo-[2.2.1]hept-2-yl, 2,6-dimethylhept-2-yl, 2,6,6-trimethylbicyclo[1.3.3]hept-2-yl, octyl, 2-octenyl, 2-methyloctan-2-yl, 2-methyl-6-methylene-7-octen-2-yl (myrcenyl), 7-methyloctan-1-yl, 3,7-dimethyl-6-octenyl, 3,7-dimethyl-7-octenyl, 3,7-dimethyl-6-octen-1-yl (citronellyl), 3,7-dimethyl-2,6-octadien-1-yl (geranyl), 3,7-dimethyl-2,6-octadien-1-yl (neryl), 3,7-dimethyl-1,6-octadien-3-yl (linalyl), 3,7-dimethyloctan-1-yl (pelagryl), 3,7-dimethyloctan-3-yl (tetrahydrolinalyl), 2,4-octadien-1-yl, 3,7-dimethyl-6-octen-3-yl, 2,6-dimethyl-7-octen-2-yl, 2,6-dimethyl-5,7-octadien-2-yl, 4,7-dimethyl-4-vinyl-6-octen-3-yl, 3-methyloctan-3-yl, 2,6-dimethyloctan-2-yl, 2,6-dimethyloctan-3-yl, 3,6-dimethyloctan-3-yl, 2,6-dimethyl-7-octen-2-yl, 2,6-dimethyl-3,5-octadien-2-yl (mugyl), 3-methyl-1-octen-3-yl, 7-hydroxy-3,7-dimethyloctanalyl, 3-nonyl, 6,8-dimethylnonan-2-yl, 3-(hydroxymethyl)-2-nonanone, 2-nonen-1-yl, 2,4-nonadien-1-yl, 2,6-nonadien-1-yl, cis-6-nonen-1-yl, 3,7-dimethyl-1,6-nonadien-3-yl, decyl, 9-decenyl, 2-benzyl-M-dioxa-5-yl, 2-decen-1-yl, 2,4-decadien-1-yl, 4-methyl-3-decen-5-yl, 3,7,9-trimethyl-1,6-decadien-3-yl (isobutyl linallyl), undecyl, 2-undecen-1-yl, 10-undecen-1-yl, 2-dodecen-1-yl, 2,4-dodecadien-1-yl, 2,7, 11-trimethyl-2,6,10-dodecatrien-1-yl (farnesyl), 3,7,11-trimethyl-1,6,10,-dodecatrien-3-yl, 3,7,11,15-tetramethylhexadec-2-en-1-yl (phytyl), 3,7,11,15-tetramethylhexadec-1-en-3-yl (iso phytol), p-methoxybenzyl (anisyl), para-cymen-7-yl (cuminyl), 4-methylbenzyl, 3,4-methylenedioxybenzyl, 2-(methyl) carboxy-1-hydroxyphenyl, 2-(benzyl)carboxy-1-hydroxyphenyl, 2-(cis-3-hexenyl)-carboxy-1-hydroxyphenyl, 2-(n-pentyl)carboxy-1-hydroxyphenyl, 2-(2-phenylethyl)carboxy-1-hydroxyphenyl, 2-(n-hexyl) carboxy-1-hydroxyphenyl, 2-methyl-5-isopropyl-1-hydroxyphenyl, 4-ethyl-2-methoxyphenyl, 4-allyl-2-methoxy-1-hydroxyphenyl (eugenyl), 2-methoxy4-(1- propenyl)-1-hydroxyphenyl (isoeugenyl), 4-allyl-2,6-dimethoxy-1-hydroxyphenyl, 4-tert-butyl-1-hydroxyphenyl, 2-ethoxy-4-methyl-1-hydroxyphenyl, 2-methyl-4-vinyl-1-hydroxyphenyl, 2-isopropyl-5-methyl-1-hydroxyphenyl (thymyl), 2-(isopentyl)-carboxy-1-hydroxyphenyl, 2-(ethyl) carboxy-1-hydroxyphenyl, 6-(methyl)carboxy-2,5-dimethyl-1,3-dihydroxyphenyl, 5-methoxy-3-methyl-1-hydroxyphenyl, 2-tert-butyl-4-methyl-1-hydroxyphenyl, 1-ethoxy-2-hydroxy-4-propenylphenyl, 4-methyl-1-hydroxyphenyl, 4-hydroxy-3-methoxybenzaldehydie, 2-ethoxy-4-hydroxybenzaldehyde, decahydro-2-naphthyl, 2,5,5-trimethyl-octahydro-2-naphthyl, 1,3,3-trimethyl-2-norbornyl (fenchyl), 3a,4,5,6,7,7a-hexahydro-2,4-dimethyl-4,7-methano-1H-inden-5-yl, 3a,4,5,6,7,7a-hexahydro-3,4-dimethyl-4,7-methano-1H-inden-5-yl, 2-methyl-2-vinyl-5-(1-hydroxy-1-methylethyl)tetrahydrofuranyl, b-caryophyllenyl, and mixtures thereof.

Most preferred $R^1$ and $R^2$ are 3,7-dimethyl-1,6-octadien-3-ol (linalool, as a racemic mixture or as each optical isomer alone), 2,6-dimethyl-7-octen-2-ol (dihydromyrcenol, as a racemic mixture or as each optical isomer alone), and mixtures thereof.

$R^3$ and $R^4$ are each independently hydrogen, methyl, ethyl, propyl, phenyl, benzyl, and mixtures thereof, preferably at least one $R^3$ or $R^4$ is not hydrogen atom, more preferably one $R^3$ or $R^4$ is hydrogen atom and the other $R^3$ or $R^4$ is methyl.

For the purposes of the present invention substituted or unsubstituted alkyleneoxy units are defined as moieties having the formula:

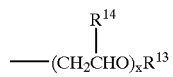

wherein $R^{13}$ is hydrogen; $R^{14}$ is hydrogen, methyl, ethyl, and mixtures thereof; the index x is from 1 to about 10.

For the purposes of the present invention substituted or unsubstituted alkyleneoxyalkyl are defined as moieties having the formula:

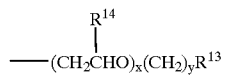

wherein $R^{13}$ is hydrogen, $C_1$–$C_{18}$ alkyl, $C_1$–$C_4$ alkoxy, and mixtures thereof; $R^{14}$ is hydrogen, methyl, ethyl, and mixtures thereof; the index x is from 1 to about 9 and the index y is from 1 to about 18.

For the purposes of the present invention substituted or unsubstituted alkylenearyl units are defined as moieties having the formula:

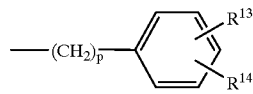

wherein $R^{13}$ and $R^{14}$ are each independently hydrogen, hydroxy, $C_1$–$C_4$ alkoxy, nitrilo, halogen, nitro, carboxyl (—CHO; —CO$_2$H; —CO$_2$R'; —CONH$_2$; —CONHR'; —CONR'$_2$; wherein R' is $C_1$–$C_{12}$ linear or branched alkyl), amino, alkylamino, and mixtures thereof, p is from 1 to about 14.

For the purposes of the present invention substituted or unsubstituted aryloxy units are defined as moieties having the formula:

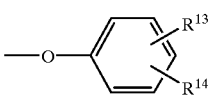

wherein $R^{13}$ and $R^{14}$ are each independently hydrogen, hydroxy, $C_1$–$C_4$ alkyl, $C_1$–$C_4$ alkoxy, nitrilo, halogen, nitro, carboxyl (—CHO; —CO$_2$H; —CO$_2$R'; —CONH$_2$; —CONHR'; —CONR'$_2$; wherein R' is $C_1$–$C_{15}$ linear or branched alkyl), amino, alkylamino, and mixtures thereof.

For the purposes of the present invention substituted or unsubstituted alkyleneoxyaryl units are defined as moieties having the formula:

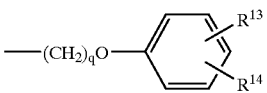

wherein $R^{13}$ and $R^{14}$ are each independently hydrogen, hydroxy, $C_1$–$C_4$ alkyl, $C_1$–$C_4$ alkoxy, nitrilo, halogen, nitro, carboxyl (—CHO; —CO$_2$H; —CO$_2$R'; —CONH$_2$; —CONHR'; —CONR'$_2$; wherein R' is $C_1$–$C_{12}$ linear or branched alkyl), amino, alkylamino, and mixtures thereof, q is from 1 to about 14.

For the purposes of the present invention substituted or unsubstituted oxyalkylenearyl units are defined as moieties having the formula:

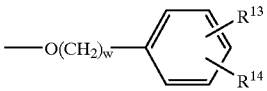

wherein $R^{13}$ and $R^{14}$ are each independently hydrogen, hydroxy, $C_1$–$C_4$ alkyl, $C_1$–$C_4$ alkoxy, nitrilo, halogen, nitro, carboxyl (—CHO; —CO$_2$H; —CO$_2$R'; —CONH$_2$; —CONHR'; —CONR'$_2$; wherein R' is $C_1$–$C_{12}$ linear or branched alkyl), amino, alkylamino, and mixtures thereof, w is from 1 to about 14.

The pro-fragrances of the present invention release "fragrance raw material alcohols" which provide a pleasurable "fresh" and/or "clean" smell or scent to fabric to which the pro-fragrances are applied. Non-limiting examples of alcohols suitably released by the hydrolysis of the orthoester pro-fragrances include methanol, 2,4-dimethyl-3-cyclohexene-1-methanol (Floralol), 2,4-dimethyl cyclohexane methanol (Dihydro floralol), 5,6-dimethyl-1-methylethenylbicyclo[2.2.1]hept-5-ene-2-methanol (Arbozol), 2,4,6-trimethyl-3-cyclohexene-1-methanol (Isocyclo geraniol), 4-(1-methylethyl)cyclohexanemethanol (Mayol), a-3,3-trimethyl-2-norborane methanol, 1,1-dimethyl-1-(4-methylcyclohex-3-enyl)methanol, ethanol, 2-phenylethanol, 2-cyclohexylethanol, 2-(o-methylphenyl)-ethanol, 2-(m-methylphenyl)ethanol, 2-(p-methylphenyl) ethanol, 6,6-dimethylbicyclo-[3.1.1]hept-2-ene-2-ethanol (nopol), 2-(4-methylphenoxy)ethanol, 3,3-dimethyl-D$^2$-b-norbornane ethanol, 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methylphenyl)ethanol, n-propanol, 2-propanol, 1-phenylpropanol, 3-phenylpropanol, 2-phenylpropanol (Hydrotropic Alcohol), 2-(cyclododecyl)propan-1-ol (Hydroxy-ambran), 2,2-dimethyl-3-(3-methylphenyl)propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), a-n-pentyl-3-phenyl-2-propen-1-ol (a-amyl-cinnamyl alcohol), ethyl-3-hydroxy-3-phenylpropionate, 2-(4-methylphenyl)-2-propenol, n-butanol, 2-butanol, 3-methylbutanol, 3-(4-methylcyclohex-3-ene)butanol, 2-methyl-4-(2,2,3-trimethyl-3-cyclopenten-1-yl)butanol, 2-ethyl-4-(2,2,3-trimethyl-cyclopent-3-enyl)-2-buten-1-ol, 3-methyl-2-buten-1-ol, 2-methyl-4-(2,2,3-trimethyl-3-cyclopenten-1-yl)-2-buten-1-ol, 3-hydroxy-2-butanone, ethyl 3-hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)butan-2-one, pentanol, cis-3-pentenol, 3-methyl-pentanol, 3-methyl-3-penten-1-ol, 2-methyl-4-phenylpentanol (Pamplefleur), 3-methyl-5-phenylpentanol (Phenoxanol), 2-methyl-5-phenylpentanol, 2-methyl-5-(2,3-dimethyltricyclo[2.2.1.0(2,6)]hept-3-yl)-2-penten-1-ol (santalol), 4-methyl-1-phenyl-2-pentanol, (1-methyl-bicyclo[2.1.1]hepten-2-yl)-2-methylpent-1-en-3-ol, 3-methyl-1-phenylpentan-3-ol, 1,2-dimethyl-3-(1-methylethenyl)cyclopentan-1-ol, 2-isopropyl-5-methyl-2-hexenol, cis-3-hexen-1-ol, trans-2-hexen-1-ol, 2-isoproenyl-4-methyl-4-hexen-1-ol (Lavandulol), 2-ethyl-2-prenyl-3-hexenol, 1-hydroxymethyl-4-iso-propenyl-1-cyclohexene (Dihydrocuminyl alcohol), 1-methyl-4-isopropenylcyclohex-6-en-2-ol (carvenol), 6-methyl-3-isopropenylcyclohexan-1-ol, 1-methyl4-iso-propenylcyclohexan-3-ol, 4-isopropyl-1-methylcyclohexan-3-ol, 4-tert-butylcyclohexanol, 2-tert-butylcyclohexanol, 2-tert-butyl-4-methylcyclohexanol, 4-isopropylcyclohexanol, 4-methyl-1-(1-methylethyl)-3-cyclohexen-1-ol, 2-(5,6,6-trimethyl-2-norbornyl)cyclohexanol, isobornylcyclohexanol, 3,3,5-trimethylcyclohexanol, 1-methyl-4-isopropylcyclohexan-3-ol, 1,2-dimethyl-3-(1-methylethyl)cyclohexan-1-ol, heptanol, 2,4-dimethylheptan-1-ol, 2,4-dimethyl-2,6-heptandienol, 6,6-dimethyl-2-oxymethylbicyclo[3.1.1]hept-2-ene (myrtenol), 4-methyl-2,4-heptadien-1-ol, 3,4,5,6,6-pentamethyl-2-heptanol, 3,6-dimethyl-3-vinyl-5-hepten-2-ol, 6,6-dimethyl-3-hydroxy-2-methylenebicyclo[3.1.1]heptane, 1,7,7-trimethylbicyclo[2.2.1]heptan-2-ol, 2,6-dimethylheptan-2-ol, 2,6,6-trimethylbicyclo[1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol (geraniol), 3,7-dimethyl-2,6-octadien-1-ol (nerol), 3,7-dimethyl-1,6-octadien-3-ol (linalool), 3,7-dimethyloctan-1-ol (pelagrol), 3,7-dimethyloctan-3-ol (tetrahydrolinalool), 2,4-octadien-1-ol, 3,7-dimethyl-6-octen-3-ol, 2,6-dimethyl-7-octen-2-ol, 2,6-dimethyl-5,7-octadien-2-ol, 4,7-dimethyl-4-vinyl-6-octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6-nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linalool), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol, 3,7,11,15-tetramethylhexadec-2-en-1-ol (phytol), 3,7,11,15-tetramethylhexadec-1-en-3-ol (iso phytol), benzyl alcohol, p-methoxy benzyl alcohol (anisyl alcohol), para-cymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl-1-hydroxybenzene, 1-ethoxy-2-hydroxy-4-propenylbenzene, 4-hydroxytoluene, 4-hydroxy-3-methoxybenzaldehyde, 2-ethoxy-4-hydroxybenzaldehyde, decahydro-2-naphthol, 2,5,5-trimethyl-octahydro-2-naphthol, 1,3,3-trimethyl-2-norbornanol (fenchol), 3a,4,5,6,7,7a-hexahydro-2,4-dimethyl-4,7-methano-1H-inden-5-ol, 3a,4,5,6,7,7a-hexahydro-3,4-dimethyl-4,7-methano-1H-inden-5-ol, 2-methyl-2-vinyl-5-(1-hydroxy-1-methylethyl) tetrahydrofuran, b-caryophyllene alcohol, and mixtures thereof.

Preferred alcohols released by the pro-fragrance compounds of the present invention are 4-(1-methylethyl)cyclohexanemethanol (mayol), 2,4-dimethyl-3-cyclohexen-1-ylmethanol (floralol), 2,4-dimethylcyclohex-1-ylmethanol (dihydrofloralol), 2,4,6-trimethyl-3-cyclohexen-1-ylmethanol (isocyclogeraniol), 2-phenylethanol, 1-(4-isopropylcyclohexyl)ethanol (mugetanol), 2-(o-methylphenyl)ethanol (ortho-hawthanol), 2-(m-methylphenyl)ethanol (meta-hawthanol), 2-(p-methylphenyl)-ethanol (para-hawthanol), 2,2-dimethyl-3-(3-methylphenyl)propan-1-ol (majantol), 3-phenyl-2-propen-1-ol (cinnamic alcohol), 2-methyl-4-(2,2,3-trimethyl-3-cyclopenten-1-yl)-2-buten-1-ol (santalaire), 3-methyl-5-phenylpentan-1-ol (phenoxanol), 3-methyl-5-(2,2,3-trimethyl-3-cyclopenten-1-yl)-4-penten-2-ol (ebanol), 2-methyl-4-phenylpentan-1-ol (pamplefleur), cis-3-hexen-1-ol, 3,7-dimethyl-6-octen-1-ol (citronellol), 3,7-dimethyl-2,6-octadien-1-ol (geraniol, nerol or mixtures thereof), 7-methoxy-3,7-dimethyloctan-2-ol (osyrol), 3,7-dimethyl-1,6-octadien 3-ol (linalool), 2,6-dimethyl-7-octen-2-ol (dihydromyrcenol), 6,8-dimethylnonan-2-ol, cis-6-nonen-1-ol, 2,6-nonadien-1-ol, 4-methyl-3-decen-5-ol (undecavertol), benzyl alcohol, 2-methoxy-4-(1-propenyl) phenol (isoeugenol), 2-methoxy-4-(2-propenyl)phenol (eugenol), 4-hydroxy-3-methoxybenzaldehyde (vanillin), and mixtures thereof. More preferably 3,7-dimethyl-1,6-octadien-3-ol (linalool), 2,6-dimethyl-7-octen-2-ol (dihydromyrcenol), and mixtures thereof.

According to the present invention all isomers of a fragrance raw material whether in the form of the pro-fragrance or the released fragrance raw material, are suitable for use in the present invention. When optical isomers are possible, fragrance raw materials may be included as either the separate chemical isomer or as the combined racemic mixture. For example, 3,7-dimethyl-6-octen-1-ol, commonly known by those of ordinary skill in the art as b-citronellol or cephrol, comprises a pair of optical isomers, R-(+)-b-citronellol and S-(−)-b-citronellol. Each of these materials separately or as a racemic pair are suitable for use as fragrance raw materials in the present invention. However, those skilled in the art of fragrances, by utilization of the present invention, should not disregard any olfactory differences that individual optical isomers impart. By way of example, carvone, 2-methyl-5-(1-methylethenyl)-2-cyclohexene-1-one exists as two isomers; d-carvone and l-carvone, d-Carvone is found in oil of caraway and renders a completely different fragrance from l-carvone which is found in spearmint oil. According to the present invention a pro-fragrance which releases d-carvone will result in a different fragrance than one which releases l-carvone. The same applies to l-carvone.

Similarly, the pro-fragrances of the present invention may form diasteriomers when more than one chiral center is present in the molecules. According to the present invention, no single isomer or isomer pair is favored over another single isomer or isomer pair, however, if the formulator chooses one isomer or pair of isomers over the other because of their fragrance "character" or other bulk property characteristic, the choice does not diminish the value of the other remaining isomer or isomer pair for the purposes of the present invention.

The ketals and acetals of the present invention can be modified by the formulator to provide highly substantive pro-fragrance compounds capable of delivering both linalool and tetrahydromyrcenol to fabric surfaces for subsequent release after the laundry process has concluded An example of a linalool-containing pro-fragrance which comprises a highly substantive moiety has the formula:

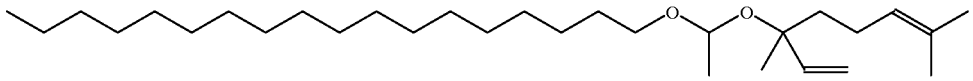

wherein an octadecyl moiety provides for increased fabric substantivity.

An example of a dihydromyrcenol-containing pro-fragrance which comprises a highly substantive moiety has the formula:

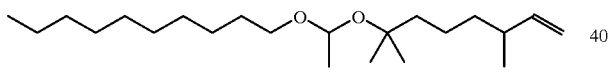

wherein a decyl moiety provides for increased fabric substantivity.

Fragrance raw materials may be too hydrophilic for direct formulation into laundry detergent compositions. The present invention provides compounds which have highly hydrophobic moieties which aid in the solublizing of the substrate as well as the substantivity. An example of a linalool-containing pro-fragrance which comprises a highly water soluble moiety has the formula:

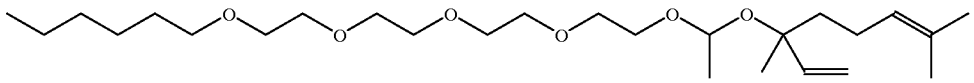

wherein a $C_6$ alkyl $E_4$ moiety provides for increase fabric substantivity.

In addition, the present invention relates to fragrance delivery systems useful in laundry detergent compositions, and rinse-added and dryer-added fabric conditioning compositions. The fragrance delivery systems of the present invention provide slow, sustained release of fragrance raw materials which provide the clothing or fabric article with a pleasant "fresh" or "clean" scent. In addition, as described herein above, the formulator may modify the pyranyl or furanyl portion of the pro-fragrance materials in order to provide increased fabric substantivity or laundry liquor solubility to the compounds which comprise the fragrance delivery system.

In general, the laundry detergent compositions of the present invention which have increased fragrance retention and fragrance longevity, comprise:

A) at least about 0.01%, preferably from about 0.01% to about 10%, more preferably from about 0.1% to about 1% by weight, of a fragrance delivery system comprising:
  ii) one or more pro-fragrance compounds of the present invention;
  iii) optionally fragrance carriers and other fragrance delivery adjuncts;
  iv) optionally one or more releasable pro-fragrance materials;

B) at least about 0.01% by weight, preferably from about 0.1% to about 60%, more preferably from about 0.1% to about 30% by weight, of a detersive surfactant selected from the group consisting of anionic, cationic, nonionic, zwitterionic, ampholytic surfactants, and mixtures thereof, preferably said surfactant is an anionic surfactant; and C) the balance carriers and adjunct ingredients said adjunct ingredients are selected from the group consisting of builders, optical brighteners, bleaches, bleach boosters, bleach catalysts, bleach activators, soil release polymers, dye transfer agents, dispersents, enzymes, suds suppressers, dyes, perfumes, colorants, tiller salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof.

For the purposes of the present invention the term "one or more releasable pro-fragrance materials" described in section A (iv) above, is defined as other compounds which can suitably release a fragrance raw material, for example, as disclosed in U.S. Pat. No. 5,378,468 Suffis et al., issued Jan. 3, 1995, incorporated herein by reference.

In general, the rinse added fabric softening compositions of the present invention which have increased fragrance retention and fragrance longevity, comprise:

A) at least about 0.01%, preferably from about 0.01% to about 10%, more preferably from about 0.1% to about 1% by weight, of a fragrance delivery system comprising:
  i) one or more pro-fragrance compounds according to the present invention;
  ii) optionally one or more fragrance raw materials;
  iii) optionally fragrance carriers and other fragrance delivery adjuncts;

B) from about 0.01%, preferably from about 85% to about 99.9% by weight of the composition, of ingredients useful for formulating fabric softening compositions, said ingredients selected from the group consisting of cationic fabric softening agents; nonionic fabric softening agents; liquid carrier; concentration aid; soil release agent; perfume; and preservatives/stabilizers, and mixtures thereof;

C) at least about 50% of a liquid carrier; and

D) optionally from about 0.01% to about 15% by weight, of concentration aids;

wherein further said compositions have a pH of less than about 6 at 20° C.

In general, the dryer-added added fabric softening and fabric appearance benefit compositions are delivered by a article of manufacture such as a substrate, preferably a flexible substrate which is added to the dryer, said articles of manufacture comprise:

A) at least about 0.01%, preferably from about 0.01% to about 10%, more preferably from about 0.1% to about 1% by weight, of a fragrance delivery system comprising:
  i) one or more pro-fragrance compounds according to the present invention;
  ii) optionally one or more fragrance raw materials;
  iii) optionally fragrance carriers and other fragrance delivery adjuncts;

B) a fabric treatment component comprising:
  a) from about 1% to about 60% by weight, of a polyamine having the formula;
    i) a polyamine having a backbone of the formula:

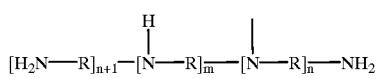

wherein R is $C_2$–$C_8$ alkylene, $C_3$–$C_8$ alkyl substituted alkylene, and mixtures thereof, preferably ethylene, 1,2-propylene, 1,3-propylene, more preferably ethylene;
    ii) a polyamine having a backbone of the formula:

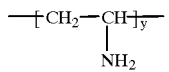

wherein y is from 5 to about 10,000; and
    iii) optionally from 0% to 100% of the polyamine backbone NH units are substituted by one or more units having the formula:

wherein $R^1$ is $C_2$–$C_6$ alkylene, $C_3$–$C_6$ alkyl substituted alkylene, and mixtures thereof; $R^2$ is hydrogen, $C_1$–$C_4$ alkyl, and mixtures thereof, preferably hydrogen and methyl; wherein m is from 2 to about 700; n is from 0 to about 350; x is from 1 to 12, preferably from 1 to about 4; y is from 5 to 5000.
  b) from about 40% to about 99% by weight, of a carboxylic acid carrier;
    wherein the fabric treatment composition has a viscosity of less than about 2000 centipoise at 100° C. and a melting point from about 25° C. to about 95° C.; and C) dispensing means which provides for release of an effective amount of said polyamine (i) and carboxylic acid carrier (ii) to fabrics in an automatic laundry dryer at operating temperatures.

Surfactant Systems

The instant cleaning compositions may contain at least about 0.01% by weight of a surfactant selected from the group consisting of anionic, cationic, nonionic, ampholytic and zwitterionic surface active agents. Preferably the solid (i.e. granular) and viscous semi-solid (i.e. gelatinous, pastes, etc.) systems of the present invention, surfactant is preferably present to the extent of from about 0.1% to 60%, more preferably 0.1% to about 30% by weight of the composition.

Nonlimiting examples of surfactants useful herein typically at levels from about 1% to about 55%, by weight, include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^-M^+)CH_3$ and $CH_3(CH_2)_y(CHOSO_3^-M^+)CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("$AE_xS$"; especially EO 1–7 ethoxy sulfates), $C_{10}$–$C_{18}$ alkyl alkoxy carboxylates (especially the EO 1–5 ethoxycarboxylates), the $C_{10}$–$C_{18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides are highly preferred, especially the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Other conventional useful surfactants are described further herein and are listed in standard texts.

Anionic surfactants can be broadly described as the water-soluble salts, particularly the alkali metal salts, of organic sulfuric reaction products having in their molecular structure an alkyl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the anionic synthetic detergents which can form the surfactant component of the compositions of the present invention are the sodium or potassium alkyl sulfates, especially those obtained by sulfating the higher alcohols (C8–18 carbon atoms) produced by reducing the glycerides of tallow or coconut oil; sodium or potassium alkyl benzene sulfonates, in which the alkyl group contains from about 9 to about 15 carbon atoms, (the alkyl radical can be a straight or branched aliphatic chain); sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid ester of the reaction product of one mole of a higher fatty alcohol (e.g. tallow or coconut alcohols) and about 1 to about 10 moles of ethylene oxide; sodium or potassium salts of alkyl phenol ethylene oxide ether sulfates with about 1 to about 10 units of ethylene oxide per molecule and in which the alkyl radicals contain from 8 to 12 carbon atoms; the reaction products of fatty acids are derived from coconut oil sodium or potassium salts of fatty acid amides of a methyl tauride in which the fatty acids, for example, are derived from coconut oil and sodium or potassium beta-acetoxy- or beta-acetamido-alkanesulfonates where the alkane has from 8 to 22 carbon atoms.

Additionally, secondary alkyl sulfates may be used by the formulator exclusively or in conjunction with other surfactant materials and the following identifies and illustrates the differences between sulfated surfactants and otherwise conventional alkyl sulfate surfactants. Non-limiting examples of such ingredients are as follows.

Conventional primary alkyl sulfates (AS), such as those illustrated above, have the general formula ROSO3-M+ wherein R is typically a linear C8–22 hydrocarbyl group and M is a water solublizing cation. Branched chain primary alkyl sulfate surfactants (i.e., branched-chain "PAS") having 8–20 carbon atoms are also know; see, for example, Eur. Pat. Appl. 439,316, Smith et al., filed Jan. 21, 1991.

Conventional secondary alkyl sulfate surfactants are those materials which have the sulfate moiety distributed randomly along the hydrocarbyl "backbone" of the molecule. Such materials may be depicted by the structure $$CH_3(CH_2)_n(CHOSO_3^-M^+)(CH_2)_mCH_3$$

wherein m and n are integers of 2 of greater and the sum of m+n is typically about 9 to 17, and M is a water-solublizing cation.

The aforementioned secondary alkyl sulfates are those prepared by the addition of $H_2SO_4$ to olefins. A typical synthesis using alpha olefins and sulfuric acid is disclosed in U.S. Pat. No. 3,234,258, Morris, issued Feb. 8, 1966 or in U.S. Pat. No. 5,075,041, Lutz, issued Dec. 24,1991. See also U.S. Pat. No. 5,349,101, Lutz et al., issued Sep. 20, 1994; U.S. Pat. No. 5,389,277, Prieto, issued Feb. 14, 1995.

The preferred surfactants of the present invention are anionic surfactants, however, other surfactants useful herein are described below.

The compositions of the present invention can also comprise at least about 0.01%, preferably at least 0.1%, more preferably from about 1% to about 30%, of an nonionic detersive surfactant. Preferred nonionic surfactants such as $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), block alkylene oxide condensate of $C_6$ to $C_{12}$ alkyl phenols, alkylene oxide condensates of $C_8$–$C_{22}$ alkanols and ethylene oxide/propylene oxide block polymers (Pluronic™-BASF Corp.), as well as semi polar non-ionics (e.g., amine oxides and phosphine oxides) can be used in the present compositions. An extensive disclosure of these types of surfactants is found in U.S. Pat. No. 3,929,678, Laughlin et al., issued Dec. 30, 1975, incorporated herein by reference.

Alkylpolysaccharides such as disclosed in U.S. Pat. No. 4,565,647 Llenado (incorporated herein by reference) are also preferred nonionic surfactants in the compositions of the invention.

More preferred nonionic surfactants are the polyhydroxy fatty acid amides having the formula:

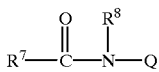

wherein $R^7$ is $C_5$–$C_{31}$ alkyl, preferably straight chain $C_7$–$C_{19}$ alkyl or alkenyl, more preferably straight chain $C_9$–$C_{17}$ alkyl or alkenyl, most preferably straight chain $C_{11}$–$C_{15}$ alkyl or alkenyl, or mixtures thereof; $R^8$ is selected from the group consisting of hydrogen, $C_1$–$C_4$ alkyl, $C_1$–$C_4$ hydroxyalkyl, preferably methyl or ethyl, more preferably methyl. Q is a polyhydroxyalkyl moiety having a linear alkyl chain with at least 3 hydroxyls directly connected to the chain, or an alkoxylated derivative thereof; preferred alkoxy is ethoxy or propoxy, and mixtures thereof. Preferred Q is derived from a reducing sugar in a reductive amination reaction. More preferably Q is a glycityl moiety. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may, yield a mix of sugar components for Q. It should be understood that it is by no means intended to exclude other suitable raw materials. Q is more preferably selected from the group consisting of $-CH_2(CHOH)_nCH_2OH$, $-CH(CH_2OH)(CHOH)_{n-1}CH_2OH$, $-CH_2(CHOH)_2-(CHOR')(CHOH)CH_2OH$, and alkoxylated derivatives thereof, wherein n is an integer from 3 to 5, inclusive, and R' is hydrogen or a cyclic or aliphatic monosaccharide. Most preferred substituents for the Q moiety are glycityls wherein n is 4, particularly $-CH_2(CHOH)_4CH_2OH$.

$R^7CO-N<$ can be, for example, cocamide, stearamide, oleamide, lauramide, myristamide, capricamide, palmitamide, tallowamide, etc.

$R^8$ can be, for example, methyl, ethyl, propyl, isopropyl, butyl, 2-hydroxy ethyl, or 2-hydroxy propyl.

Q can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

A particularly desirable surfactant of this type for use in the compositions herein is alkyl-N-methyl glucomide, a compound of the above formula wherein $R^7$ is alkyl (preferably $C_{11}$–$C_{17}$), $R^8$, is methyl and Q is 1-deoxyglucityl.

Other sugar-derived surfactants include the N-alkoxy polyhydroxy fatty acid amides, such as $C_{10}$–$C_{18}$ N-(3-methoxypropyl)glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used.

ADJUNCT INGREDIENTS

Builders—Detergent builders can optionally be included in the compositions herein to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least about 1% builder. Formulations typically comprise from about 5% to about 50%, more typically about 5% to about 30%, by weight, of detergent builder. Granular formulations typically comprise from about 10% to about 80%, more typically from about 15% to about 50% by weight, of the detergent builder. Lower or higher levels of builder, however, are not meant to be excluded.

Inorganic or P-containing detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a $SiO_2:Na_2O$ ratio in the range 1.6:1 to 3.2:1 and layered silicates, such as the layered sodium silicates described in U.S. Pat. No. 4,664,839, issued May 12, 1987 to H. P. Rieck. NaSKS-6 is the trademark for a crystalline layered silicate marketed by Hoechst (commonly abbreviated herein as "SKS-6"). Unlike zeolite builders, the Na SKS-6 silicate builder does not contain aluminum. NaSKS-6 has the delta-$Na_2SiO_5$ morphology form of layered silicate. It can be prepared by methods such as those described in German DE-A-3,417,649 and DE-A-3,742,043. SKS-6 is a highly preferred layered silicate for use herein, but other such layered silicates, such as those having the general formula $NaMSi_xO_{2x+1} \cdot yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the alpha, beta and gamma forms. As noted above, the delta-$Na_2SiO_5$ (NaSKS-6 form) is most preferred for use herein. Other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates as disclosed in German Patent Application No. 2,321,001 published on Nov. 15, 1973.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

$$[M_z(zAlO_2)_y] \cdot xH_2O$$

wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula:

$$Na_{12}[(AlO_2)_{12}(SiO_2)_{12}] \cdot xH_2O$$

wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysticcinic acid, and soluble salts thereof.

Citrate builders, e.g., citric acid and soluble salts thereof (particularly sodium salt), are polycarboxylate builders of particular importance for heavy duty liquid detergent formulations due to their availability from renewable resources and their biodegradability. Citrates can also be used in granular compositions, especially in combination with zeolite and/or layered silicate builders. Oxydisuccinates are also especially useful in such compositions and combinations.

Also suitable in the detergent compositions of the present invention are the 3,3-dicarboxy4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also Diehl U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity.

Such use of fatty acids will generally result in a diminution of sudsing, which should be taken into account by the formulator.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Clay Soil Removal/Anti-redeposition Agents

The compositions of the present invention can also optionally contain water-soluble ethoxylated amines having clay soil removal and antiredeposition properties. Granular detergent compositions which contain these compounds typically contain from about 0.01% to about 10.0% by weight of the water-soluble ethoxylates amines; liquid detergent compositions typically contain about 0.01% to about 5%.

The most preferred soil release and anti-redeposition agent is ethoxylated tetraethylenepentamine. Exemplary ethoxylated amines are further described in U.S. Pat. No. 4,597,898, VanderMeer, issued Jul. 1, 1986. Another group of preferred clay soil removal-antiredeposition agents are the cationic compounds disclosed in European Patent Application 111,965, Oh and Gosselink, published Jun. 27, 1984. Other clay soil removal/antiredeposition agents which can be used include the ethoxylated amine polymers disclosed in European Patent Application 111,984, Gosselink, published Jun. 27, 1984; the zwitterionic polymers disclosed in European Patent Application 112,592, Gosselink, published Jul. 4, 1984; and the amine oxides disclosed in U.S. Pat. No. 4,548,744, Connor, issued Oct. 22, 1985. Other clay soil removal and/or anti redeposition agents known in the art can also be utilized in the compositions herein. Another type of preferred antiredeposition agent includes the carboxy methyl cellulose (CMC) materials. These materials are well known in the art.

Other Ingredients—A wide variety of other ingredients useful in detergent compositions can be included in the compositions herein, including other active ingredients, carriers, hydrotropes, processing aids, dyes or pigments, solid fillers for bar compositions, etc. Other optional ingredients include enzymes, bleaches, bleach activators, bleach catalysts, photoactivators, dyes, fluorescers, fabric conditioners, hydrolyzable surfactants, optical brighteners, preservatives, anti-oxidants, chelants, stabilizers, anti-shrinkage agents, anti-wrinkle agents, soil release agents, germicides, fungicides, and anti corrosion agents. If high sudsing is desired, suds boosters such as the $C_{10}$–$C_{16}$ alkanolamides can be incorporated into the compositions, typically at 1%–10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, 0.1%–2%, to provide additional suds and to enhance grease removal performance.

Various detersive ingredients employed in the present compositions optionally can be further stabilized by absorbing said ingredients onto a porous hydrophobic substrate, then coating said suostrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT D10, DeGussa) is admixed with a proteolytic enzyme solution containing 3%–5% of $C_{13-15}$ ethoxylated alcohol (EO 7) nonionic surfactant. Typically, the enzyme/surfactant solution is 2.5× the weight of silica. The resulting powder is dispersed with stirring in silicone oil (various silicone oil viscosity in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergent compositions.

The detergent compositions herein will preferably be formulated such that, during use in aqueous cleaning operations, the wash water will have a pH of between about 6.5 and about 11, preferably between about 7.5 and 10.5. Laundry products are typically at pH 9–11. Techniques for controlling pH at recommended usage levels include the use of buffers, alkalis, acids, etc., and are well known to those skilled in the art.

Granular Compositions

The pro-accords of the present invention can be used in both low density (below 550 grams/liter) and high density granular compositions in which the density of the granule is at least 550 grams/liter. Granular compositions are typically designed to provide an in the wash pH of from about 7.5 to about 11.5, more preferably from about 9.5 to about 10.5. Low density compositions can be prepared by standard spray-drying processes. Various means and equipment are available to prepare high density compositions. Current commercial practice in the field employs spray-drying towers to manufacture compositions which have a density less than about 500 g/l. Accordingly, if spray-drying is used as part of the overall process, the resulting spray-dried particles must be further densified using the means and equipment described hereinafter. In the alternative, the formulator can eliminate spray-drying by using mixing, densifying and granulating equipment that is commercially available. The following is a nonlimiting description of such equipment suitable for use herein.

Various means and equipment are available to prepare high density (i.e., greater than about 550, preferably greater than about 650, grams/liter or "g/l"), high solubility, free-flowing, granular detergent compositions according to the present invention. Current commercial practice in the field employs spray-drying towers to manufacture granular laundry detergents which often have a density less than about 500 g/l. In this procedure, an aqueous slurry of various heat-stable ingredients in the final detergent composition are formed into homogeneous granules by passage through a spray-drying tower, using conventional techniques, at temperatures of about 175° C. to about 225° C. However, if spray drying is used as part of the overall process herein, additional process steps as described hereinafter must be used to obtain the level of density (i.e., >650 g/l) required by modem compact, low dosage detergent products.

For example, spray-dried granules from a tower can be densified further by loading a liquid such as water or a nonionic surfactant into the pores of the granules and/or subjecting them to one or more high speed mixer/densifiers. A suitable high speed mixer/densifier for this process is a device marketed under the tradename "Lödige CB 30" or "Lödige CB 30 Recycler" which comprises a static cylindrical mixing drum having a central rotating shaft with mixing/cutting blades mounted thereon. In use, the ingredients for the detergent composition are introduced into the drum and the shaft/blade assembly is rotated at speeds in the range of 100–2500 rpm to provide thorough mixing/densification. See Jacobs et al, U.S. Pat. No. 5,149,455, issued Sep. 22, 1992. The preferred residence time in the high speed mixer/densifier is from about 1 to 60 seconds. Other such apparatus includes the devices marketed under the tradename "Shugi Granulator" and under the tradename "Drais K-TTP 80).

Another process step which can be used to densify further spray-dried granules involves grinding and agglomerating or deforming the spray-dried granules in a moderate speed mixer/densifier so as to obtain particles having lower intra-particle porosity. Equipment such as that marketed under the tradename "Lödige KM" (Series 300 or 600) or "Lödige Ploughshare" mixer/densifiers are suitable for this process step. Such equipment is typically operated at 40–160 rpm. The residence time of the detergent ingredients in the moderate speed mixer/densifier is from about 0.1 to 12 minutes. Other useful equipment includes the device which is available under the tradename "Drais K-T 160". This process step which employs a moderate speed mixer/densifier (e.g. Lödige KM) can be used by itself or sequentially with the aforementioned high speed mixer/densifier (e.g. Lödige CB) to achieve the desired density. Other types of granules manufacturing apparatus useful herein include the apparatus disclosed in U.S. Pat. No. 2,306,898, to G. L. Heller, Dec. 29, 1942.

While it may be more suitable to use the high speed mixer/densifier followed by the low speed mixer/densifier, the reverse sequential mixer/densifier configuration is also contemplated by the invention. One or a combination of various parameters including residence times in the mixer/densifiers, operating temperatures of the equipment, temperature and/or composition of the granules, the use of adjunct ingredients such as liquid binders and flow aids, can be used to optimize densification of the spray-dried granules in the process of the invention. By way of example, see the processes in Appel et al, U.S. Pat. No. 5,133,924, issued Jul. 28, 1992 (granules are brought into a deformable state prior to densification); Delwel et al, U.S. Pat. No. 4,637,891, issued Jan. 20, 1987 (granulating spray-dried granules with a liquid binder and aluminosilicate); Kruse et al, U.S. Pat. No. 4,726,908, issued Feb. 23, 1988 (granulating spray-dried granules with a liquid binder and aluminosilicate); and, Bortolotti et al, U.S. Pat. No. 5,160,657, issued Nov. 3, 1992 (coating densified granules with a liquid binder and aluminosilicate).

In those situations in which particularly heat sensitive or highly volatile detergent ingredients or pro-accords are to be incorporated into the final detergent composition, processes which do not include spray drying towers are preferred. The formulator can eliminate the spray-drying step by feeding, in either a continuous or batch mode, starting detergent ingredients directly into mixing/densifying equipment that is commercially available. One particularly preferred embodiment involves charging a surfactant paste and an anhydrous builder material into a high speed mixer/densifier (e.g. Lödige CB) followed by a moderate speed mixer/densifier (e.g. Lödige KM) to form high density detergent agglomerates. See Capeci et al, U.S. Pat. No. 5,366,652, issued Nov. 22, 1994 and Capeci et al, U.S. Pat. No. 5,486,303, issued Jan. 23, 1996. Optionally, the liquid/solids ratio of the starting detergent ingredients in such a process can be selected to obtain high density agglomerates that are more free flowing and crisp.

Optionally, the process may include one or more recycle streams of undersized particles produced by the process which are fed back to the mixer/densifiers for further agglomeration or build-up. The oversized particles produced by this process can be sent to grinding apparatus and then fed back to the mixing/densifying equipment. These additional recycle process steps facilitate build-up agglomeration of the starting detergent ingredients resulting in a finished composition having a uniform distribution of the desired particle size (400–700 microns) and density (>550 g/l). See Capeci et al, U.S. Pat. No. 5,516,448, issued May 14, 1996 and Capeci et al, U.S. Pat. No. 5,489,392, issued Feb. 6, 1996. Other suitable processes which do not call for the use of spray-drying towers are described by Bollier et al, U.S. Pat. No. 4,828,721, issued May 9, 1989; Beerse et al, U.S. Pat. No. 5,108,646, issued Apr. 28, 1992; and, Jolicoeur, U.S. Pat. No. 5,178,798, issued Jan. 12, 1993.

In yet another embodiment, the high density detergent composition of the invention can be produced using a fluidized bed mixer. In this process, the various ingredients of the finished composition are combined in an aqueous slurry (typically 80% solids content) and sprayed into a fluidized bed to provide the finished detergent granules. Prior to the fluidized bed, this process can optionally include the step of mixing the slurry using the aforementioned Lödige CB mixer/densifier or a "Flexomix 160" mixer/densifier, available from Shugi. Fluidized bed or moving beds of the type available under the tradename "Escher Wyss" can be used in such processes.

Another suitable process which can be used herein involves feeding a liquid acid precursor of an anionic surfactant, an alkaline inorganic material (e.g. sodium carbonate) and optionally other detergent ingredients into a high speed mixer/densifier (residence time 5–30 seconds) so as to form agglomerates containing a partially or totally neutralized anionic surfactant salt and the other starting detergent ingredients. Optionally, the contents in the high, speed mixer/densifier can be sent to a moderate speed mixer/densifier (e.g. Lödige KM) for further agglomeration resulting in the finished high density detergent composition. See Appel et al, U.S. Pat. No. 5,164,108, issued Nov. 17, 1992.

OPTIONAL FABRIC CONDITIONING AGENTS AND ADJUNCTS

Adjunct Cationic Conditioning Agents

Compositions of the present invention can contain from about 5% to about 95%, preferably from about 15% to about 90%, more preferably from about 25% to about 85%, and even more preferably from about 25% to about 55%, of biodegradable cationic softener, preferably an ester quaternary ammonium compound (EQA).

The optional fabric conditioning component is preferably a fabric softening compound which is an ester quaternary ammonium (EQA) compound or its precursor amine having the formula:

Formula I

wherein Y is a carboxy moiety having the formula

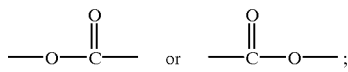

the index p is from 1 to 3; the index v is from 1 to 4, and mixtures thereof; $R^1$ is $C_1$–$C_6$ alkyl, $C_1$–$C_4$ hydroxy alkyl group, or benzyl, preferably $C_1$–$C_3$ alkyl, for example, methyl, ethyl, propyl, most preferred is methyl; preferably one $R^1$ moiety is a short chain alkyl group, preferably methyl; $R^2$ is $C_8$–$C_{30}$ saturated alkyl or $C_8$–$C_{30}$ unsaturated alkyl, $C_8$–$C_{30}$ substituted alkyl or $C_8$–$C_{30}$ unsubstituted alkyl, preferably $C_{14}$–$C_{18}$ saturated alkyl or $C_{14}$–$C_{18}$ unsaturated alkyl, $C_{14}$–$C_{18}$ substituted alkyl or $C_{14}$–$C_{18}$ unsubstituted alkyl, more preferably linear $C_{14}$–$C_{18}$ saturated alkyl, wherein each $R^2$ moiety suitable for use has an Iodine Value of from about 3 to about 60; the counter ion, $X^-$, can be any softener-compatible anion, preferably methylsulfate, ethylsulfate, chloride, bromide, formate, sulfate, lactate, nitrate, benzoate, more preferably methylsulfate.

Tallow is a convenient and inexpensive source of long chain alkyl and alkenyl materials.

It will be understood that substituents $R^1$ and $R^2$ of Formula I can optionally be substituted with various groups such as alkoxyl or hydroxyl groups. The preferred compounds can be considered to be diester (DEQA) variations of ditallow dimethyl ammonium methyl sulfate (DTDMAMS), which is a widely used fabric softener. At least 80% of the DEQA is in the diester form, and from 0% to about 20%, preferably less than about 10%, more preferably less than about 5%, can be EQA monoester (e.g., only one —Y—$R^2$ group).

The following are non-limiting examples of EQA Formula I (wherein all long-chain alkyl substituents are straight-chain):

Saturated $[C_2H_5]_2{}^+N[CH_2CH_2OC(O)C_{17}H_{35}]_2(CH_3SO_4)^-$
$[CH_3][C_2H_5]^+N[CH_2CH_2OC(O)C_{13}H_{27}]_2[HC(O)O]^-$
$[C_3H_7][C_2H_5]^+N[CH_2CH_2OC(O)C_{11}H_{23}]_2(CH_3SO_4)^-$
$[CH_3]_2{}^+N-[CH_2CH_2OC(O)C_{17}H_{35}]CH_2CH_2OC(O)C_{15}H_{31}(CH_3SO_4)^-$
$[CH_3]_2{}^+N[CH_2CH_2OC(O)R^2]_2(CH_3SO_4)^-$
where —C(O)$R^2$ is derived from saturated tallow.

Unsaturated $[CH_3]_2{}^+N[CH_2CH_2OC(O)C_{17}H_{33}]_2(CH_3SO_4)^-$
$[C_2H_5]_2{}^+N[CH_2CH_2OC(O)C_{17}H_{33}]_2Cl^-$
$[CH_3][C_2H_5]^+N[CH_2CH_2OC(O)C_{13}H_{25}]_2[C_6H_5C(O)O]^-$
$[CH_3]_2{}^+N-[CH_2CH_2OC(O)C_{17}H_{33}]CH_2CH_2OC(O)C_{15}H_{29}(CH_3SO_4)^-$
$[CH_3]_2{}^+N[CH_2CH_2OC(O)R^2]_2(CH_3SO_4)^-$
where —C(O)$R^2$ is derived from partially hydrogenated tallow or modified tallow having the characteristics set forth herein.

Other specific examples of biodegradable Formula I compounds suitable for use in the fabric softening compositions herein are:

N-methyl-N,N-di-(2-$C_{14}$–$C_{18}$-acyloxy ethyl);
N-2-hydroxyethyl ammonium methylsulfate;
$[HOCH(CH_3)CH_2][CH_3]^+N[CH_2CH_2OC(O)C_{15}H_{31}]_2Br^-$;
$[HOCH(CH_3)CH_2][CH_3]^+N[CH_2CH_2OC(O)C_{15}H_{29}]_2[HC(O)O]^-$; and $[CH_2CH_2OH][CH_3]^+N[CH_2CH_2OC(O)R^{21}]_2(CH_3SO_4)^-$.
A preferred compound is N-methyl, N,N-di-(2-oleyloxyethyl) N-2-hydroxyethyl ammonium methyl sulfate.

Further suitable fabric softening compounds are quaternary ammonium compounds having the formula:

Formula II

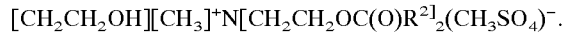

wherein Y" is a carboxy moiety having the formula

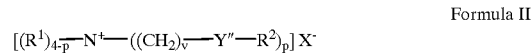

and mixtures thereof, wherein at least one Y" group is

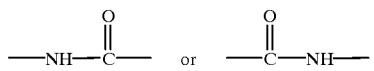

the index p is from 1 to 3; the index v is from 1 to 4, and mixtures thereof; $R^1$ is $C_1$–$C_6$ alkyl or benzyl, preferably $C_1$–$C_3$ alkyl, for example, methyl, ethyl, propyl, most preferred is methyl; preferably one $R^1$ moiety is a short chain alkyl group, preferably methyl; $R^2$ is $C_8$–$C_{30}$ saturated alkyl or $C_8$–$C_{30}$ unsaturated alkyl, $C_8$–$C_{30}$ substituted alkyl or $C_8$–$C_{30}$ unsubstituted alkyl, preferably $C_{14}$–$C_{18}$ saturated alkyl or $C_{14}$–$C_{18}$ unsaturated alkyl, $C_{14}$–$C_{18}$ substituted alkyl or $C_{14}$–$C_{18}$ unsubstituted alkyl, more preferably linear $C_{14}$–$C_{18}$ saturated alkyl, wherein each $R^2$ moiety suitable for use has an Iodine Value of from about 3 to about 60; $R^3$ is R or H; the counter ion, $X^-$, can be any softener-compatible anion, preferably methylsulfate, ethylsulfate, chloride, bromide, formate, sulfate, lactate, nitrate, benzoate, more preferably methylsulfate.

It will be understood that substituents R and $R^2$ of Formula II can optionally be substituted with various groups such as alkoxyl or hydroxyl groups.

The preferred ester linked compounds (DEQA) can be considered to be diester variations of ditallow dimethyl ammonium chloride (DTDMAC), which is a widely used fabric softener. Preferably, at least 80% of the DEQA is in the diester form, and from 0% to about 20%, preferably less than about 10%, more preferably less than about 5%, can be DEQA monoester (e.g., only one —Y—$R^2$ group). For optimal antistatic benefit monoester should be low, preferably less than about 2.5%. The level of monoester can be controlled in the manufacturing of the DEQA.

The quaternary softening compounds with at least partially unsaturated alkyl or acyl groups have advantages (i.e., antistatic benefits) and are highly acceptable for consumer products when certain conditions are met. Antistatic effects are especially important where the fabrics are dried in a tumble dryer, and/or where synthetic materials which generate static are used. Any reference to IV values hereinafter refers to IV of fatty alkyl or acyl groups and not to the resulting quaternary, e.g., DEQA compound. As the IV is raised, there is a potential for odor problems.

For unsaturated softener actives, the optimum storage temperature for stability and fluidity depends on the specific IV of, e.g., the fatty acid used to make DEQA and/or the level/type of solvent ;elected. Exposure to oxygen should be minimized to keep the unsaturated groups frown oxidizing. It can therefore be important to store the material under a reduced oxygen atmosphere such as a nitrogen blanket. It is important to provide good molten storage stability to provide a commercially feasible raw material that will not degrade noticeably in the normal transportation/storage/handling of the material in manufacturing operations.

The following are non-limiting examples of DEQA Formula II (wherein all long-chain alkyl substituents are straight-chain):

Saturated

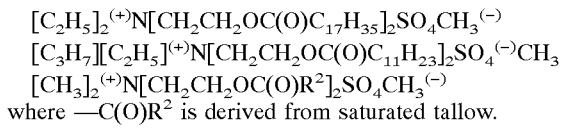

where $-C(O)R^2$ is derived from saturated tallow.

Unsaturated

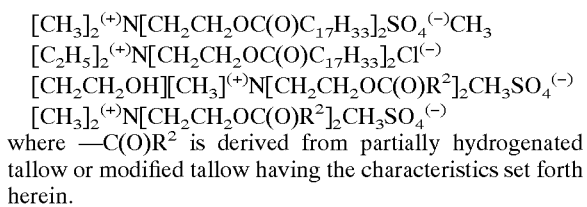

where $-C(O)R^2$ is derived from partially hydrogenated tallow or modified tallow having the characteristics set forth herein.

Further suitable fabric softening compounds according to the present invention are ester quaternary ammonium compounds having the formula:

Formula III

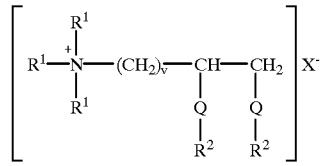

wherein Q is a carboxy moiety having the formula

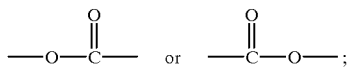

the index v is from 1 to 4, and mixtures thereof; $R^1$ is $C_1-C_4$ alkyl, $C_1-C_4$ hydroxy alkyl group, preferably methyl; preferably one $R^1$ moiety is a short chain alkyl group, a preferably methyl; $R^2$ is $C_8-C_{30}$ saturated alkyl or $C_8-C_{30}$ unsaturated alkyl, $C_8-C_{30}$ substituted alkyl or $C_8-C_{30}$ unsubstituted alkyl, preferably $C_{14}-C_{18}$ saturated alkyl or $C_{14}-C_{18}$ unsaturated alkyl, $C_{14}-C_{18}$ substituted alkyl or $C_{14}-C_{18}$ unsubstituted alkyl, more preferably linear $C_{14}-C_{18}$ saturated alkyl, wherein each $R^2$ moiety suitable for use has an Iodine Value of from about 3 to about 60; the counter ion $X^-$ is methylsulfate.

An example of the above described ester quaternary ammonium compound which is suitable for use as a fabric softening compound in the present invention is 1,2-bis (tallowyloxy)-3-trimethyl ammoniopropane methylsulfate (DTTMAPMS). Other suitable examples are 1,2-bis (cocoyloxy)-3-trimethyl ammoniopropane methylsulfate, 1,2-bis(lauryloxy)-3-trimethyl ammoniopropane methylsulfate, 1,2-bis(oleyloxy)-3-trimethyl ammoniopropane methylsulfate and 1,2-bis(stearyloxy)-3-trimethyl ammoniopropane meehylsulfate. Replacing one or more or the methyl moieties in the above examples with ethyl, propyl, isopropyl, butyl, isobutyl, or mixtures thereof, result in suitable fabric softening compounds according to the present invention. In addition, other anions other than methylsulfate may be used.

Other examples of suitable Formula III EQA compounds of this invention are obtained by, e.g., replacing "tallowyl" in the above compounds with, for example, cocoyl, lauryl, oleyl, stearyl, palmityl, or the like; replacing "methyl" in the above compounds with ethyl, propyl, isopropyl, butyl, isobutyl, t-butyl, or the hydroxy substituted analogs of these radicals; replacing "methylsulfate" in the above compounds with chloride, ethylsulfate, bromide, formate, sulfate, lactate, nitrate, and the like, but methylsulfate is preferred.

Yet still further suitable fabric softening compounds according to the present invention are ester quaternary ammonium compounds having the formula:

Formula IV

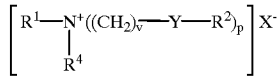

wherein Y is a carboxy moiety having the formula

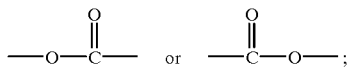

the index p is 2; the index v is from 1 to 4, and mixtures thereof; $R^1$ is $C_1-C_4$ alkyl or hydroxy alkyl, preferably $C_1-C_3$ alkyl, for example, methyl, ethyl, propyl, most preferred is methyl; $R^2$ is $C_8-C_{30}$ saturated or unsaturated, substituted or unsubstituted alkyl having an Iodine Value of from about 3 to about 60, preferred $R^2$ is $C_8-C_{14}$ linear or branched alkyl, more preferred $C_8-C_{14}$ linear alkyl; $R^4$ is a $C_1-C_4$ alcohol; the counter ion, $X^-$, can be any softener-compatible anion, preferably methylsulfate, ethylsulfate, chloride, bromide, formate, sulfate, lactate, nitrate, benzoate, more preferably methyl sulfate.

Most preferably, the quaternary ammonium compound is a fully saturated compound, such as diniethyl bis (tallowyloxyethyl)ammonium methylsulfate, derived from hardened tallow. Also suitable are dimethyl bis (acyloxyethyl)ammonium methylsulfate derivatives of $C_8-C_{30}$ fatty acids, such as dimethyl bis(tallowyloxyethyl) ammonium methylsulfate; dimethyl bis(oleyloxyethyl) ammonium methylsulfate or dimethyl bis(cocoyloxyethyl) ammonium methylsulfate. The composition of the present invention may comprise from about 15% to about 90% of these quaternary ammonium compounds.

An example of the above described ester quaternary ammonium compounds suitable for use as a fabric softening compound according to the present invention is N-methyl-N,N-bis-(2-$C_{14}$-$C_{18}$-acyloxy)ethyl-N-2-hydroxyethyl ammonium methylsulfate. A preferred example is N-methyl-N,N-bis(2-oleyloxyethyl)-N-(2-hydroxyethyl)ammonium methylsulfate.

The fabric conditioning composition can be any of those known in the art and/or previously disclosed by others in patent applications. Compositions that are suitable are disclosed in U.S. Pat. No.: 3,944,694, McQueary; U.S. Pat. No. 4,073,996, Bedenk et al.; U.S. Pat. No. 4,237,155, Kardouche; U.S. Pat. No. 4,711,730 Gosselink et al.; U.S. Pat. No. 4,749,596, Evans et al.; U.S. Pat. No. 4,808,086, Evans et al.; U.S. Pat. No. 4,818,569, Trinh et al.; U.S. Pat. No.

4,877,896, Maldonado et al.; U.S. Pat. No. 4,976,879, Maldonado et al.; U.S. Pat. No. 5,041,230, Borcher, Sr. et al.; U.S. Pat. No. 5,094,761, Trinh et al.; U.S. Pat. No. 5,102,564, Gardlik et al.; and U.S. Pat. No. 5,234,610, Gardlik et al., all of said patents being incorporated herein by reference.

The compounds herein can be prepared by standard esterification and quaternization reactions, using readily available starting materials. General methods for preparation are disclosed in U.S. Pat. No. 4,137,180, incorporated herein by reference.

As used herein, when the diester quat is specified, it will include the monoester quat that is normally present. For the optimal antistatic benefit the percentage of monoester quat should be as low as possible, preferably less than about 20%. The level of monoester quat present can be controlled in the manufacturing of the EQA.

EQA compounds prepared with fully saturated acyl groups are rapidly biodegradable and excellent softeners. However, it has been discovered that compounds prepared with at least partially unsaturated acyl groups have advantages (i.e., antistatic benefits) and are highly acceptable for consumer products when certain conditions are met.

Variables that must be adjusted to obtain the benefits of using unsaturated acyl groups include the Iodine Value (IV) of the fatty acids, the odor of fatty acid starting material, and/or the EQA. Any reference to IV values herein refers to IV of fatty acyl groups and not to the resulting EQA compound.

Antistatic effects are especially important where the fabrics are dried in a tumble dryer, and/or where synthetic materials which generate static are used. As the IV is raised, there is a potential for odor problems.

Some highly desirable, readily available sources of fatty acids such as tallow, possess odors that remain with the compound EQA despite the chemical and mechanical processing steps which convert the raw tallow to finished EQA. Such sources must be deodorized, e.g., by absorption, distillation (including stripping such as steam stripping), etc., as is well known in the art. In addition, care should be taken to minimize the adverse results of contact of the resulting fatty acyl groups with oxygen and/or bacteria by adding antioxidants, antibacterial agents, etc. The additional expense and effort associated with the unsaturated fatty acyl groups is justified by the superior performance.

Generally, hydrogenation of fatty acids to reduce polyunsaturation and to lower IV to insure good color and odor stability leads to a high degree of trans configuration in the molecule. Therefore, diester compounds derived from fatty acyl groups having low IV values can be made by mixing fully hydrogenated fatty acid with touch hydrogenated fatty acid at a ratio which provides an IV of from about 3 to about 60. The polyunsaturation content of the touch hardened fatty acid should be less than about 5%, preferably less than about 1%. During touch hardening the cis/trans isomer weight ratios are controlled by methods known in the art such as by optimal mixing, using specific catalysts, providing high $H_2$ availability, etc.

It has also been found that for good chemical stability of the diester quaternary compound in molten storage, water levels in the raw material must be minimized to preferably less than about 1% and more preferably less than about 0.5%. Storage temperatures should be kept as low as possible and still maintain a fluid material, ideally in the range of from about 49° C. to about 75° C. The optimum storage temperature for stability and fluidity depends on the specific IV of the fatty acid used to make the diester quaternary and the level/type of solvent selected. Also, exposure to oxygen should be minimized to keep the unsaturated groups from oxidizing. It can therefore be important to store the material under a reduced oxygen atmosphere such as a nitrogen blanket. It is important to provide good molten storage stability to provide a commercially feasible raw material that will not degrade noticeably in the normal transportation/storage/handling of the material in manufacturing operations.

Adjunct fabric softening compositions employed herein contain as an optional component, at a level of from about 0% to about 95%, preferably from about 20% to about 75%, more preferably from about 20% to about 60%, a carboxylic acid salt of a tertiary amine and/or ester amine which has the formula:

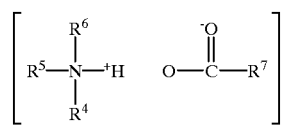

wherein $R^5$ is a long chain aliphatic group containing from about 8 to about 30 carbon atoms; $R^4$ and $R^6$ are the same or different and are independently selected from the group consisting of aliphatic groups containing from about 1 to about 30 carbon atoms, hydroxyalkyl groups of the formula $R^8OH$ wherein $R^8$ is an alkylene group of from about 2 to about 30 carbon atoms, and polyalkyleneoxy moieties of the formula $R^9O(R^{10}O)_m$— wherein $R^9$ is hydrogen, $C_1$–$C_{30}$ alkyl, $C_1$–$C_{30}$ alkenyl, and mixtures thereof; $R^{10}$ is ethylene, 1,2 propylene, 1,3-propylene, and mixtures thereof; m is from about 2 to about 10; wherein further the $R^4$, $R^5$, $R^6$, $R^8$, and $R^9$ chains can be ester interrupted groups; and wherein $R^7$ is selected from the group consisting of $C_2$–$C_{30}$ linear alkyl, $C_2$–$C_{30}$ linear alkenyl, $C_8$–$C_{30}$ aryl, $C_8$–$C_{30}$ alkylaryl, and $C_8$–$C_{30}$ arylalkyl; substituted $C_1$–$C_{30}$ linear alkyl, $C_1$–$C_{30}$ linear alkenyl, $C_8$–$C_{30}$ aryl, $C_8$–$C_{30}$ alkylaryl, and $C_8$–$C_{30}$ arylalky wherein the substituents are selected from the group consisting of halogen, carboxyl, and hydroxyl, said composition having a thermal softening point of from about 35° C. to about 100° C.

Preferably, $R^5$ is an aliphatic chain containing from about $C_{12}$–$C_{30}$ linear alkyl, $R^6$ is $C_{12}$–$C_{30}$ linear alkyl, and $R^4$ is $C_1$–$C_{30}$ linear alkyl.

Examples of preferred tertiary aminos as starting material for the reaction between the amine and carboxylic acid to form the tertiary amine salts are: lauryldimethylamine, myristyldimethylamine, stearyldimethylamine, tallowdimethylamine, coconutdimethylamine, dilaurylmethylamine, distearylmethylamine, ditallowmethylamine, oleyldimethylamine, dioleylmethylamine, lauryldi(3-hydroxypropyl)amine, stearyldi(2-hydroxyethyl)amine, trilaurylamine, laurylethylmethylamine, and

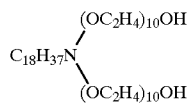

Preferred fatty acids are those wherein $R^7$ is $C_8$–$C_{30}$ linear alkyl, more preferably $C_{11}$–$C_{17}$ linear alkyl.

Examples of specific carboxylic acids as a starting material are: formic acid, acetic acid, lauric acid, myristic acid, palmitic acid, stearic acid, oleic acid, oxalic acid, adipic acid, 12-hydroxy stearic acid, benzoic acid, 4-hydroxy benzoic acid, 3-chloro benzoic acid, 4-nitro benzoic acid, 4-ethyl benzoic acid, 4-(2-chloroethyl)benzoic acid, phenylacetic acid, (4-chlorophenyl)acetic acid, (4-hydroxyphenyl) acetic acid, and phthalic acid.

Preferred carboxylic acids are stearic, oleic, lauric, myristic, palmitic, and mixtures thereof.

The amine salt can be formed by a simple addition reaction, well known in the art, disclosed in U.S. Pat. No. 4,237,155, Kardouche, issued Dec. 2, 1980, which is incorporated herein by reference. Excessive levels of free amines may result in odor problems, and generally free amines provide poorer softening performance than the amine salts.

Preferred amine salts for use herein as optional ingredients are those wherein the amine moiety is a $C_8$–$C_{30}$ alkyl or alkenyl dimethyl amine or a di-$C_8$–$C_{30}$ alkyl or alkenyl methyl amine, and the acid moiety is a $C_8$–$C_{30}$ alkyl or alkenyl monocarboxylic acid. The amine and the acid, respectively, used to form the amine salt will often be of mixed chain lengths rather than single chain lengths, since these materials are normally derived from natural fats and oils, or synthetic processed which produce a mixture of chain lengths. Also, it is often desirable to utilize mixtures of different chain lengths in order to modify the physical or performance characteristics of the softening composition.

Specific preferred amine salts for use in the present invention are oleyldimethylamine stearate, stearyldimethylamine stearate, stearyldimethylamine myristate, stearyldimethylamine oleate, stearyldimethylamine palmitate, distearylmethylamine palmitate, distearylmethylamine laurate, and mixtures thereof. A particularly preferred mixture is oleyldimethylamine stearate and distearylmethylamine myristate, in a ratio of 1:10 to 10:1, preferably about 1:1.

Adjunct Nonionic Conditioning Agents

An optional softening agent of the present invention is a nonionic fabric softener material. Typically, such nonionic fabric softener materials have an HLB of from about 2 to about 9, more typically from about 3 to about 7. In general, the materials selected should be relatively crystalline, higher melting, (e.g., >25° C.).

The level of optional nonionic softener in the solid composition is typically from about 10% to about 50%, preferably from about 15% to about 40%.

Preferred nonionic softeners are fatty acid partial esters of polyhydric alcohols, or anhydrides thereof, wherein the alcohol, or anhydride, contains from about 2 to about 18, preferably from about 2 to about 8, carbon atoms, and each fatty acid moiety contains from about 8 to about 30, preferably from about 12 to about 20, carbon atoms. Typically, such softeners contain from about one to about 3, preferably about 2 fatty acid groups per molecule.

The polyhydric alcohol portion of the ester can be ethylene glycol, glycerol, poly (e.g., di-, tri-, tetra, penta-, and/or hexa-) glycerol, xylitol, sucrose, erythritol, penta-erythritol, sorbitol or sorbitan.

The fatty acid portion of the ester is normally derived from fatty acids having from about 8 to about 30, preferably from about 12 to about 22, carbon atoms. Typical examples of said fatty acids being lauric acid, myristic acid, palmitic acid, stearic acid, oleic acid, and behenic acid.

Highly preferred optional nonionic softening agents for use in the present invention are $C_{10}$–$C_{26}$ acyl sorbitan esters and polyglycerol monostearate. Sorbitan esters are esterified dehydration products of sorbitol. The preferred sorbitan ester comprises a member selected from the group consisting of $C_{10}$–$C_{26}$ acyl sorbitan monoesters and $C_{10}$–$C_{26}$ acyl sorbitan diesters and ethoxylates of said esters wherein one or more of the unesterified hydroxyl groups in said esters contain from 1 to about 6 oxyethylene units, and mixtures thereof. For the purpose of the present invention, sorbitan esters containing unsaturation (e.g., sorbitan monooleate) can be utilized.

Sorbitol, which is typically prepared by the catalytic hydrogenation of glucose, can be dehydrated in well known fashion to form mixtures of 1,4- and 1,5-sorbitol anhydrides and small amounts of isosorbides. (See U.S. Pat. No. 2,322,821, Brown, issued Jun. 29, 1943, incorporated herein by reference.)

The foregoing types of complex mixtures of anhydrides of sorbitol are collectively referred to herein as "sorbitan." It will be recognized that this "sorbitan" mixture will also contain some free, uncyclized sorbitol.

The preferred sorbitan softening agents of the type employed herein can be prepared by esterifying the "sorbitan" mixture with a fatty acyl group in standard fashion, e.g., by reaction with a fatty acid halide, fatty acid ester, and/or fatty acid. The esterification reaction can occur at any of the available hydroxyl groups, and various mono-, di-, etc., esters can be prepared. In fact, mixtures of mono-, di-, tri-, etc., esters almost always result from such reactions, and the stoichiometric ratios of the reactants can be simply adjusted to favor the desired reaction product.

For commercial production of the sorbitan ester materials, etherification and esterification are generally accomplished in the same processing step by reacting sorbitol directly with fatty acids. Such a method of sorbitan ester preparation is described more fully in MacDonald; "Emulsifiers:" Processing and Quality Control:, *Journal of the American Oil Chemists' Society*, Vol. 45, October 1968.

Details, including formula, of the preferred sorbitan esters can be found in U.S. Pat. No. 4,128,484, incorporated hereinbefore by reference.

Certain derivatives of the preferred sorbitan esters herein, especially the "lower" ethoxylates thereof (i.e., mono-, di-, and tri-esters wherein one or more of the unesterified —OH groups contain one to about twenty oxyethylene moieties (Tweens®) are also useful in the composition of the present invention. Therefore, for purposes of the present invention, the term "sorbitan ester" includes such derivatives.

The material which is sold commercially as sorbitan mono-ester (e.g., monostearate) does in fact contain significant amounts of di- and tri-esters and a typical analysis of sorbitan monostearate indicates that it comprises about 27% mono-, 32% di- and 30% tri- and tetra-esters. Commercial sorbitan monostearate therefore is a preferred material. Mixtures of sorbitan stearate and sorbitan palmitate having stearate/palmitate weight ratios varying between 10:1 and 1:10, and 1,5-sorbitan esters are useful. Both the 1,4- and 1,5-sorbitan esters are useful herein.

Other useful alkyl sorbitan esters for use in the softening compositions herein include sorbitan monlaurate, sorbitan monomyristate, sorbitan monopalmitate, sorbitan monobehenate, sorbitan monooleate, sorbitan dilaurate, sorbitan dimyristate, sorbitan dipalmitate, sorbitan distearate, sorbitan dibehenate, sorbitan dioleate, and mixtures thereof, and mixed tallowalkyl sorbitan mono- and di-esters. Such mixtures are readily prepared by reacting the foregoing hydroxy-substituted sorbitans, particularly the 1,4- and 1,5-sorbitans, with the corresponding acid, ester, or acid chloride in a simple esterification reaction. It is to be recognized, of course, that commercial materials prepared in this manner will comprise mixtures usually containing minor proportions of uncyclized sorbitol, fatty acids, polymers, isosorbide structures, and the like. In the present invention, it is preferred that such impurities are present at as low a level as possible.

The preferred sorbitan esters employed herein can contain up to about 15% by weight of esters of the $C_{20}$–$C_{26}$, and higher, fatty acids, as well as minor amounts of $C_8$, and lower, fatty esters.

Glycerol and polyglycerol esters, especially glycerol, diglycerol, triglycerol, and polyglycerol mono- and/or di-esters, preferably mono-, are also preferred herein (e.g., polyglycerol monostearate with a trade name of Radiasurf 7248). Glycerol esters can be prepared from naturally occurring triglycerides by normal extraction, purification and/or inter-esterification processes or by esterification processes of the type set forth hereinbefore for sorbitan esters. Partial esters of glycerin can also be ethoxylated to form usable derivatives that are included within the term "glycerol esters."

Useful glycerol and polyglycerol esters include mono-esters with stearic, oleic, palmitic, lauric, isostearic, myristic, and/or behenic acids and the diesters of stearic, oleic, palmitic, lauric, isostearic, behenic, and/or myristic acids. It is understood that the typical mono-ester contains some di- and tri-ester, etc.

The "glycerol esters" also include the polyglycerol, e.g., diglycerol through octaglycerol esters. The polyglycerol polyols are formed by condensing glycerin or epichlorohydrin together to link the glycerol moieties via ether linkages. The mono- and/or diesters of the polyglycerol polyols are preferred, the fatty acyl groups typically being those described hereinbefore for the sorbitan and glycerol esters.

The dryer activated fabric softening compositions of the present invention may further includes a co-softener. The co-softener may comprise a carboxylic acid salt of a tertiary amine, tertiary amine ester, or mixtures thereof. The carboxylic acid salt forming anion moiety of the co-softener may be selected from the group consisting of lauric, myristic, palmitic, stearic, oleic and mixtures thereof. The amine salt of the co-softener may be selected from the group consisting of oleyldimethylamine stearate, dioleylmethylamine stearate, linoleyldimethylamine stearate, dilinoleylmethylamine stearate, stearyldimethylamine stearate, distearylmethylamine myristate, stearyldimethylamine palmitate, distearylmethylamine palmitate, distearylmethylamine myristate, distearyl-methylamine palmitate, distearylmethylamine laurate, dioleyldistearylmethylamine oleate, distearylmethyl-amine oleate, and mixtures thereof.

Optional Cyclodextrin/Perfume Complexes and Free Perfume

The products herein can also contain from about 0.5% to about 60%, preferably from about 1% to about 50%, cyclodextrin/perfume inclusion complexes and/or free perfume, as disclosed in U.S. Pat. No. 5,139,687, Borcher et al., issued Aug. 18, 1992; and U.S. Pat. No. 5,234,610, Gardlik et al., to issue Aug. 10, 1993, which are incorporated herein by reference. Perfumes are highly desirable, can usually benefit from protection, and can be complexed with cyclodextrin. Fabric softening products typically contain perfume to provide an olfactory aesthetic benefit and/or to serve as a signal that the product is effective.

The optional perfume ingredients and compositions of this invention are the conventional ones known in the art. Selection of any perfume component, or amount of perfume, is based solely on aesthetic considerations. Suitable perfume compounds and compositions can be round in the art including U.S. Pat. No. : 4,145,184, Brain and Cummins, issued Mar. 20, 1979; U.S. Pat. No. 4,209,417, Whyte, issued Jun. 24, 1980; U.S. Pat. No. 4,515,705, Moeddel, issued May 7, 1985; and U.S. Pat. No. 4,152,272, Young, issued May 1, 1979, all of said patents being incorporated herein by reference. Many of the art recognized perfume compositions are relatively substantive to maximize their odor effect on substrates. However, it is a special advantage of perfume delivery via the perfume/cyclodextrin complexes that non-substantive perfumes are also effective.

If a product contains both free and complexed perfume, the escaped perfume from the complex contributes to the overall perfume odor intensity, giving rise to a longer lasting perfume odor impression.

As disclosed in U.S. Pat. No. 5,234,610, Gardlik/Trinh/Banks/Benvegnu, issued Aug. 3, 1993, said patent being incorporated herein by reference, by adjusting the levels of free perfume and perfume/CD complex it is possible to provide a wide range of unique perfume profiles in terms of timing (release) and/or perfume identity (character). Solid, dryer-activated fabric conditioning compositions are a uniquely desirable way to apply the cyclodextrins, since they are applied at the very end of a fabric treatment regimen when the fabric is clean and when there are almost no additional treatments that can remove the cyclodextrin.

Stabilizers

Stabilizers can be present in the compositions of the present invention. The term "stabilizer," as used herein, includes antioxidants and reductive agents. These agents are present at a level of from 0% to about 2%, preferably from about 0.01% to about 0.2%, more preferably from about 0.05% to about 0.1% for antioxidants and more preferably from about 0.01% to about 0.2% for reductive agents. These assure good odor stability under long term storage conditions for the compositions. Use of antioxidants and reductive agent stabilizers is especially advantageous for low scent products (low perfume).

Examples of antioxidants that can be added to the compositions of this invention include a mixture of ascorbic acid, ascorbic palmitate, propyl gallate, available from Eastman Chemical Products, Inc., under the trade names Tenox® PG and Tenox S-1; a mixture of BHT, BHA, propyl gallate, and citric acid available from Eastman Chemicals Products, Inc., under the trade name Tenox-6; butylated hydroxytoluene, available from UOP Process Division under the trade name Sustane® BHT; tertiary butylhydroquinone, Eastman Chemical Products, Inc., as Tenox TBHQ; natural tocopherols, Eastman Chemical Products, Inc., as Tenox GT-1/GT-2; and butylated hydroxyanisole, Eastman Chemical Products, Inc., as BHA.

Examples of reductive agents include sodium borohydride, hypophosphorous acid, and mixtures thereof.

Other Adjunct Ingredients

The present invention can include other adjunct components (minor components) conventionally used in textile treatment compositions, for example, colorants, perfumes, perfume systems, preservatives, optical brighteners, opacifiers, stabilizers such as guar gum and polyethylene glycol, anti-shrinkage agents, anti-wrinkle agents, fabric crisping agents, spotting agents, germicides, fungicides, anti-corrosion agents, antifoam agents, and the like.

SUBSTRATE ARTICLES

In preferred embodiments, the present invention encompasses articles of manufacture. Representative articles are those that are adapted to soften fabrics in an automatic laundry dryer, of the types disclosed in U.S. Pat. No. 3,989,631, Marsan, issued Nov. 2, 1976; U.S. Pat. No. 4,055,248, Marsan, issued Oct. 25, 1977; U.S. Pat. No. 4,073,996, Bedenk et al., issued Feb. 14, 1978; U.S. Pat. No. 4,022,938, Zaki et al., issued May 10, 1977; U.S. Pat. No. 4,764,289, Trinh, issued Aug. 16, 1988; U.S. Pat. No. 4,808,086, Evans et al., issued Feb. 28,1989; U.S. Pat. No. 4,000,340, Murphy et al., issued Dec. 28, 1976; U.S. Pat. No. 4,103,047, Zaki et al., issued Jul. 25, 1978; U S. Pat. No. 3,736,668, Dillarstone, issued Jun. 5, 1973; U.S. Pat. No. 3,701,202, Compa et al., issued Oct. 31, 1972; U.S. Pat. No. 3,634,947, Furgal, issued Jan. 18, 1972; U.S. Pat. No. 3,633,538, Hoeflin, issued Jan. 11, 1972; U.S. Pat. No. 3,435,537, Rumsey, issued Apr. 1, 1969; all of which are incorporated herein by reference.

EXAMPLE 1

Preparation of Linalyl Decyl Acetaldehyde Acetal

Linalool (5.15 g, 32.4 mmol) is charged to a 25 mL round-bottomed flask fitted with a magnetic stirrer and argon inlet tube, n-Decyl vinyl ether (5.41 g, 62.4 mmol) and phosphorous oxychlonde (approximately 2 drops) are added to the flask. The mixture is stirred at room temperature for approximately 18 hr. and then treated with trimethylamine (5 drops, 25% in water). The resulting oil is purified by passing the crude material over silica gel and eluting with hexane/4% ethyl acetate to yield a colorless oil.

EXAMPLE 2

Preparation of Dihydromyrcenyl Decyl Acetaldehyde Acetal

Dihydromyrcenol (5.15 g, 64.0 mmol) is charged to a 250 mL round-bottomed flask fitted with a magnetic stirrer and argon inlet tube, n-Decyl vinyl ether (11.79 g, 64.0 mmol) and phosphorous oxychloride (approximately 5 drops) are added to the flask. The mixture is stirred at room temperature for approximately 18 hr. and then treated with triethylamine (1 mL). The resulting oil is purified by passing the crude material over silica gel and eluting with hexane/5% ethyl acetate to yield a light yellow oil.

EXAMPLE 3

Preparation of Linalyl 2-ethylhexyl Acetaldehyde Acetal

Linalool (30.00 g, 194.5 mmol) is charged to a 250 mL round-bottomed flask fitted with a magnetic stirrer and argon inlet tube. 2-Ethylhexyl vinyl ether (24.94 g, 159.6 mmol) and phosphorous oxychloride (approximately 1 drop) are added to the flask. The mixture is stirred at room temperature for approximately 72 hr. then treated with triethylamine (approximately 10 drops). The resulting oil is purified by passing the crude material over silica gel and eluting with hexane/5% ethyl acetate to yield a light yellow oil.

EXAMPLE 4

Preparation of Dihydromyrcenyl 2-ethylhexyl Acetaldehyde Acetal

Dihydromyrcenol (60.00 g, 0.384 mol) is charged to a 250 mL round-bottomed flask fitted with a magnetic stirrer and argon inlet tube. 2-Ethylhexyl vinyl ether (30.00 g, 0.192 mol) and phosphorous oxychloride (approximately 2 drops) are added to the flask. The mixture is stirred at room temperature for approximately 48 hr. then treated with triethylamine (10 drops). The resulting oil is purified by passing the crude material over silica gel and eluting with hexane/1% ethyl acetate to yield a light yellow oil.

EXAMPLE 5

Preparation of Linalyl Cyclohexyl Acetaldehyde Acetal

Linalool (60.00 g, 0.389 mol) is charged to a 250 mL round-bottomed flask fitted with a magnetic stirrer and argon inlet tube. Cyclohexyl vinyl ether (24.54 g 0.195 mol) and phosphorous oxychloride (approximately 2 drops) are added to the flask. The mixture is stirred at room temperature for 2 hr. then treated with triethylamine (approximately 10 drops). The resulting oil is purified by passing the crude material over silica gel and eluting with hexane/1% ethyl acetate to yield a light yellow oil.

EXAMPLE 6

Preparation of Linalyl Octadecyl Acetaldehyde Acetal

Linalool (7.06 g, 44.4 mmol) is placed into a 50 mL round-bottomed flask fitted with a magnetic stirrer and argon inlet tube. Octadecyl vinyl ether (24.54 g, 0.195 mol) and pyridinium p-toluenesulphonate (25 mg) are added to the flask. The mixture is stirred at room temperature for approximately 18 hr. then treated with triethylamine (approximately 10 drops). The resulting oil is purified by passing the crude material over silica gel and eluting with hexane/2% ethyl acetate to yield a light yellow oil.

EXAMPLE 7

Preparation of Linalyl Butyl Acetaldehyde Acetal

Linalool (60.00 g, 0.389 mol) is charged to a 250 mL round-bottomed flask fitted with a magnetic stirrer and argon inlet tube, n-Butyl vinyl ether (19.48 g, 0.195 mol) and phosphorous oxychloride (approximately 2 drops) are added to the flask. The mixture is stirred at room temperature for 2 hr. then treated with triethylamine (approximately 10 drops). The resulting oil is purified by passing the crude material over silica gel and eluting with hexane/1% ethyl acetate to yield a light yellow oil, and then is purified by column chromatography (elution with 1% ethyl ether dissolved in hexane) to give a light yellow oil.

EXAMPLE 8

Preparation of Didecyl Acetaldehyde Acetal

Decyl alcohol (4.62 g, 29.2 mmol) is placed into a 25 mL round-bottomed flask fitted with a magnetic stirrer and argon inlet tube, n-Decyl vinyl ether(5.97 g, 29.2 mmol) and phosphorous oxychloride (approximately 2 drops) are added to the flask. The mixture is stirred at room temperature for approximately 5 hr. then treated with triethylamine (approximately 6 drops). The resulting oil is purified by passing the crude material over silica gel and eluting with hexane/4% ethyl acetate to yield a light yellow oil.

EXAMPLES 9–17

The following are examples of granular detergent compositions comprising the pro-fragrances of the present invention.

TABLE I

| Ingredient | \multicolumn{4}{c}{weight %} | | | |
|---|---|---|---|---|
| | 9 | 10 | 11 | 12 |
| Sodium $C_{11}$–$C_{13}$ alkylbenzenesulfonate | 13.3 | 13.7 | 10.4 | 11.1 |
| Sodium $C_{14}$–$C_{15}$ alcohol sulfate | 3.9 | 4.0 | 4.5 | 11.2 |
| Sodium $C_{14}$–$C_{15}$ alcohol ethoxylate (0.5) sulfate | 2.0 | 2.0 | 0.0 | 0.0 |
| Sodium $C_{14}$–$C_{15}$ alcohol ethoxylate (6.5) | 0.5 | 0.5 | 0.5 | 1.0 |
| Tallow fatty acid | 0.0 | 0.0 | 0.0 | 1.1 |
| Sodium tripolyphosphate | 0.0 | 41.0 | 0.0 | 0.0 |
| Zeolite A, hydrate (0.1–10 micron size) | 26.3 | 0.0 | 21.3 | 28.0 |
| Sodium carbonate | 23.9 | 12.4 | 25.2 | 16.1 |
| Sodium Polyacrylate (45%) | 3.4 | 0.0 | 2.7 | 3.4 |
| Sodium silicate (1:6 ratio $NaO/SiO_2$)(46%) | 2.4 | 6.4 | 2.1 | 2.6 |
| Sodium sulfate | 10.5 | 10.9 | 8.2 | 15.0 |
| Sodium perborate | 1.0 | 1.0 | 5.0 | 0.0 |
| Poly(ethyleneglycol), MW ~4000 (50%) | 1.7 | 0.4 | 1.0 | 1.1 |
| Citric acid | 0.0 | 0.0 | 3.0 | 0.0 |
| Nonyl ester of sodium p-hydroxybenzenesulfonate | 0.0 | 0.0 | 5.9 | 0.0 |
| Soil release polymer[1] | 1.5 | 0.0 | 0.0 | 0.0 |
| Soil release polymer[2] | 0.0 | 1.5 | 0.0 | 0.0 |
| Soil release polymer[3] | 0.0 | 0.5 | 0.5 | 0.5 |
| Pro-fragrance[4] | 1.0 | 1.5 | 0.0 | 0.0 |
| Pro-fragrance[5] | 0.0 | 0.0 | 2.5 | 1.5 |
| Minors[6] | 7.0 | 2.1 | 4.1 | 6.3 |

[1]Soil release polymer according to U.S. Pat. No. 4,968,451, Scheibel et al., issued Nov. 6, 1990.
[2]Soil release polymer according to U.S. Pat. No. 5,415,807, Gosselink, Pan, Kellett and Hall, issued May 16, 1995.
[3]Soil release polymer according to U.S. Pat. No. 4,702,857, Gosselink, issued Oct. 27, 1987.
[4]Pro-fragrance according to Example 1.
[5]Pro-fragrance according to Example 2.
[6]Balance to 100% can, for example, include minors like optical brightener, perfume, suds suppressor, soil dispersant, protease, lipase, cellulase, chelating agents, dye transfer inhibiting agents, additional water, and fillers, including $CaCO_3$, talc, silicates. etc.

The following are examples of liquid laundry detergent compositions comprising pro-fragrances of the present invention.

TABLE II

| Ingredients | \multicolumn{5}{c}{Weight %} | | | | |
|---|---|---|---|---|---|
| | 13 | 14 | 15 | 16 | 17 |
| Polyhydroxy coco-fatty acid amide | 3.50 | 3.50 | 3.15 | 3.50 | 3.00 |
| NEODOL 23-9[1] | 2.00 | 0.60 | 2.00 | 0.60 | 0.60 |
| $C_{25}$ Alkyl ethoxylate sulphate | 19.00 | 19.40 | 19.00 | 17.40 | 14.00 |
| $C_{25}$ Alkyl sulfate | — | — | — | 2.85 | 2.30 |
| $C_{10}$-Aminopropylamide | — | — | — | 0.75 | 0.50 |
| Citric acid | 3.00 | 3.00 | 3.00 | 3.00 | 3.00 |
| Tallow fatty acid | 2.00 | 2.00 | 2.00 | 2.00 | 2.00 |
| Ethanol | 3.41 | 3.47 | 3.34 | 3.59 | 2.93 |
| Propanediol | 6.22 | 6.35 | 6.21 | 6.56 | 5.75 |
| Monomethanol amine | 1.00 | 0.50 | 0.50 | 0.50 | 0.50 |
| Sodium hydroxide | 3.05 | 2.40 | 2.40 | 2.40 | 2.40 |
| Sodium p-toluene sulfonate | 2.50 | 2.25 | 2.25 | 2.25 | 2.25 |
| Borax | 2.50 | 2.50 | 2.50 | 2.50 | 2.50 |
| Protease[2] | 0.88 | 0.88 | 0.88 | 0.88 | 0.88 |
| Lipolase[3] | 0.04 | 0.12 | 0.12 | 0.12 | 0.12 |
| Duramyl[4] | 0.10 | 0.10 | 0.10 | 0.10 | 0.40 |
| CAREZYME | 0.053 | 0.053 | 0.053 | 0.053 | 0.053 |
| Optical Brightener | 0.15 | 0.15 | 0.15 | 0.15 | 0.15 |
| Pro-fragrance[5] | 1.18 | 1.18 | 1.18 | 1.18 | 1.75 |
| Soil release agent[6] | 0.22 | 0.15 | 0.15 | 0.15 | 0.15 |
| Fumed silica | 0.119 | 0.119 | 0.119 | 0.119 | 0.119 |
| Minors, aesthetics, water | balance | balance | balance | balance | balance |

[1]$C_{12}$–$C_{13}$ alkyl E9 ethoxylate as sold by Shell Oil Co.
[2]*Bacillus amyloliquefaciens* subtilisin as described in WO 95/10615 published Apr. 20, 1995 by Genencor International.
[3]Derived from *Humicola lanuginosa* and commercially available from Novo.
[4]Disclosed in WO 9510603 A and available from Novo.
[5]Pro-fragrance according to Example 3.
[6]Terephthalate co-polymer as disclosed in U.S. Pat. No. 4,968,451, Scheibel et al., issued Nov. 6, 1990.

EXAMPLE 18

The following is an example of a solid bleaching composition which comprises a pro-fragrance according to the present invention.

TABLE III

| Ingredients | weight % |
|---|---|
| Nonanoyloxybenzene sulfonate | 7.0 |
| Sodium perborate | 20.0 |
| DTPA[1] | 10.0 |
| Citric acid (coated) | 20.0 |
| Fragrance[2] | 1.0 |
| Pro-fragrance[3] | 2.0 |
| Sodium sulfate | balance |

[1]Diethylenetriamine pentaacetic acid.
[2]Dihydromycenol.
[3]Pro-fragrance according to Example 4.

EXAMPLE 19

The following is an example of a liquid bleaching composition comprising a pro-accord of the present invention.

TABLE IV

| Ingredients | weight % |
|---|---|
| Sodium hypochlorite | 5.25 |
| $C_{12}$ Dimethylamine oxide | 0.9 |
| Optical brightener[1] | 0.3 |
| Fragrance[2] | 1.0 |
| Pro-fragrance[3] | 2.0 |
| Sodium hydroxide | 1.0 |
| Water | balance |

[1]4,4-bis(4-phenyl-2-H-1,2,3-triazolyl)-(2)-stilbene-2,2-disulfonic acid dipotassium salt.
[2]A mixture of linalool (20%), tetrahydrolinalool (30%), Galaxolide (30%), and citral dimethylacetal (20%).
[3]Pro-fragrance according to Examples 3 and 5 (1:1 mixture).

TABLE V

The following are examples of fabric conditioning compositions which comprise the pro-fragrances of the present invention.

| | Weight % | | | | |
|---|---|---|---|---|---|
| Ingredients | 20 | 21 | 22 | 23 | 24 |
| DEQA | 2.6 | 2.9 | 18.0 | 19.0 | 19.0 |
| Fatty acid | 0.3 | — | 1.0 | — | — |
| Hydrochloride acid | 0.02 | 0.02 | 0.02 | 0.02 | 0.02 |
| PEG | — | — | 0.6 | 0.6 | 0.6 |
| Pro-fragrance[1] | 1.0 | 1.0 | 1.0 | 1.0 | 1.0 |
| Silicone antifoam | 0.01 | 0.01 | 0.01 | 0.01 | 0.01 |
| PEI 1200 E1[2] | 2.0 | 2.0 | 1.0 | 1.5 | 2.5 |
| Dye (ppm) | 10 | 10 | 50 | 50 | 50 |
| Water and minors | balance | balance | balance | balance | balance |

[1]Pro-fragrance according to Example 7.
[2]PE 1200 E1 according to U.S. Pat. No. 5,565,145, Watson et al., issued Oct. 15, 1996.

TABLE VI

The following are examples of fabric conditioning compositions which comprise the pro-fragrances of the present invention.

| | Weight % | | | |
|---|---|---|---|---|
| Ingredients | 25 | 26 | 27 | 28 |
| Polyhydroxy Coco-Fatty Acid Amide | 3.65 | 3.50 | — | — |
| $C_{12}$–$C_{13}$ Alcohol Ethoxylate E9 | 3.65 | 0.80 | — | — |
| Sodium $C_{12}$–$C_{15}$ Alcohol Sulfate | 6.03 | 2.50 | — | — |
| DTDMAMS | 1.00 | 1.00 | 3.00 | 3.00 |
| PEI 1200 E1[1] | 4.00 | 4.00 | 4.00 | 4.00 |
| Pro-fragrance[2] | 1 | 1 | 1 | 1 |
| Perfume/Cyclodextrin Complex | — | 20 | — | 20 |
| Digeranyl Succinate | 1 | 0.50 | 1 | 1 |
| Carriers and minors | balance | balance | balance | balance |

[1]PE 1200 E1 according to U.S. Pat. No. 5,565,145, Watson et al., issued Oct. 15, 1996.
[2]Pro-fragrance according to Example 8.

What is claimed is:

1. A laundry detergent composition having increased fragrance retention and fragrance longevity, comprising:

A) At least about 0.01% by weight, of a fragrance delivery system comprising:
  i) a pro-fragrance compound having the formula:

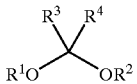

wherein at least one $R^1$ or $R^2$ is linalool, dihydromyrcenol, and mixtures thereof, and the other $R^1$ or $R^2$ is independently:
  a) $C_8$–$C_{22}$ linear or branched alkyl;
  b) $C_8$–$C_{22}$ linear or branched alkenyl;
  c) $C_2$–$C_{20}$ substituted or unsubstituted alkyleneoxy;
  d) $C_3$–$C_{20}$ substituted or unsubstituted alkyleneoxyalkyl;
  e) $C_7$–$C_{20}$ substituted or unsubstituted alkylenearyl;
  f) $C_6$–$C_{20}$ substituted or unsubstituted aryloxy;
  g) $C_7$–$C_{20}$ substituted or unsubstituted alkyleneoxyaryl;
  h) $C_7$–$C_{20}$ oxyalkylenearyl;
  i) $C_2$–$C_{20}$ alkylenecarboxy having the formula:

—$(CH_2)_xR^9$ wherein $R^9$ is —CHO, —$CO_2$M; —$CO_2R^{10}$, —$CONH_2$, —$CONHR^{10}$, —$CONR^{10}R^{11}$, and mixtures thereof; wherein $R^{10}$ and $R^{11}$ are each independently $C_1$–$C_{12}$ linear or branched alkyl, M is hydrogen or a salt forming cation, x is an integer from 1 to 19;
  j) an anionic unit having the formula:

—$(CH_2)_yR^{12}$ wherein $R^{12}$ is —$SO_3$M, —$OSO_3$M, —$PO_3$M, $OPO_3$M, or mixtures thereof; wherein M is hydrogen, one or more salt forming cations sufficient to satisfy charge balance, or mixtures thereof; y is an integer from 1 to about 22;
  k) and mixtures thereof;
  $R^3$ and $R^4$ are each independently hydrogen, methyl, ethyl, propyl, phenyl, benzyl, and mixtures thereof;
  ii) optionally one or more fragrance raw materials;
  iii) optionally fragrance carriers and other fragrance delivery adjuncts;

B) At least about 0.01% by weight, of a detersive surfactant selected from the group consisting of anionic, cationic, nonionic, zwitterionic, ampholytic surfactants, and mixtures thereof, and C) the balance carriers and adjunct ingredients.

2. A composition according to claim 1 further comprising from about 1% to about 60% by weight, of a polyamine having the formula:

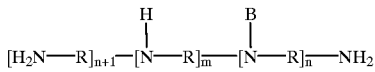

wherein R is $C_2$–$C_8$ alkylene, $C_3$–$C_8$ alkyl substituted alkylene, and mixtures thereof; B is a continuation of the backbone by branching.

3. A composition according to claim 2 comprising from about 0.01% to about 10% by weight, of a fragrance delivery system.

4. A composition according to claim 3 comprising from about 0.1% to about 1% by weight, of a fragrance delivery system.

5. A composition according to claim 2 comprising from about 0.1% to about 60% by weight, of a detersive surfactant.

6. A composition according to claim 5 comprising from about 0.1% to about 30% by weight, of a detersive surfactant.

7. A composition according to claim 2 wherein said surfactant is an anionic surfactant.

8. A composition according to claim 7 wherein R is ethylene, 1,2-propylene, 1,3-propylene.

9. A composition according to claim 8 wherein R is ethylene.

10. A composition according to claim 1 wherein said other $R^1$ or $R^2$ is:
  a) $C_8$–$C_{12}$ linear or branched alkyl;
  b) $C_8$–$C_{12}$ linear or branched alkenyl;
  c) $C_2$–$C_{12}$ substituted or unsubstituted alkyleneoxy:
  d) $C_3$–$C_{12}$ substituted or unsubstituted alkyleneoxyalkyl;

e) $C_7$–$C_{12}$ substituted or unsubstituted alkylenearyl;
f) $C_6$–$C_{10}$ substituted or unsubstituted alkyloxy;
g) $C_8$–$C_{12}$ substituted or unsubstituted alkyleneoxyaryl;
h) $C_7$–$C_{11}$ oxyalkylenearyl;
i) $C_2$–$C_{12}$ alkylenecarboxy having the formula:

—(CH$_2$)$_x$R$^9$ wherein R$^9$ is —C—HO, —CO$_2$M; —CO$_2$R$^{10}$, —CONH$_2$, —CONHR$^{10}$, —CONR$^{10}$R$^{11}$, and mixtures thereof; wherein R$^{10}$ and R$^{11}$ are each independently methyl or ethyl; $C_1$–$C_{12}$ linear or branched alkyl, M is sodium or potassium, x is an integer from 1 to 19.

11. A composition according to claim 10 wherein said other R$^1$ or R$^2$ is:
a) $C_8$–$C_{12}$ linear or branched alkyl;
b) $C_8$–$C_{12}$ linear or branched alkenyl;
c) $C_2$–$C_6$ substituted or unsubstituted alkyleneoxy;
d) $C_3$–$C_6$ substituted or unsubstituted alkyleneoxyalkyl;
e) $C_7$ substituted or unsubstituted alkylenearyl;
f) $C_6$ (substituted or unsubstituted aryloxy;
g) $C_8$ substituted or unsubstituted alkylcacoxyaryl;
h) $C_7$ oxyalkylenearyl;
i) $C_2$–$C_6$ alkylenecarboxy having the formula:

—(CH$_2$)$_x$R$^9$ wherein R$^9$ and x are the same as defined herein above.

12. A composition according to claim 1 wherein said adjunct ingredients are selected from the group consisting of builders, optical brighteners, bleaches, bleach boosters, bleach catalysts, bleach activators, soil release polymers, dye transfer agents, dispersents, enzymes, suds suppressers, dyes, perfumes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof.

13. A compound having the formula:

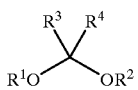

wherein R$^1$ and R$^2$ are each selected from the group consisting of linalool, myrcenol, dihydromyrcenol, and mixture thereof; R$^3$ and R$^4$ are each independently methyl, ethyl, and mixtures thereof.

14. A compound according to claim 13 wherein R$^3$ and R$^4$ are each methyl.

15. A laundry detergent composition having increased fragrance retention and fragrance longevity, comprising:
A) At least about 0.01% by weight, of a fragrance delivery system comprising:
i) a pro-fragrance compound having the formula:

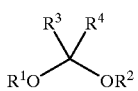

wherein R$^1$ and R$^2$ are each independently:
a) $C_8$–$C_{22}$ linear or branched alkyl;
b) $C_8$–$C_{22}$ linear or branched alkenyl;
c) $C_2$–$C_{20}$ substituted or unsubstituted alkyleneoxy;
d) $C_3$–$C_{20}$ substituted or unsubstituted alkyleneoxyalkyl;
e) $C_7$–$C_{20}$ substituted or unsubstituted alkylenearyl;
f) $C_6$–$C_{20}$ substituted or unsubstituted aryloxy;
g) $C_7$–$C_{20}$ substituted or unsubstituted alkyleneoxyaryl;
h) $C_7$–$C_{20}$ oxyalkylenearyl;
i) $C_2$–$C_{20}$ alkylenecarboxy having the formula:

—(CH$_2$)$_x$R$^9$ wherein R$^9$ is —CHO, —CO$_2$M; —CO$_2$R$^{10}$, —CONH$_2$, —CONHR$^{10}$, —CONR$^{10}$R$^{11}$, and mixtures thereof; wherein R$^{10}$ and R$^{11}$ are each independently $C_1$–$C_{12}$ linear or branched alkyl, M is hydrogen or a salt forming cation, x is an integer from 1 to 19;
j) an anionic unit having the formula:

—(CH$_2$)$_y$R$^{12}$ wherein R$^{12}$ is —SO$_3$M, —OSO$_3$M, —PO$_3$M, —OPO$_3$M, or mixtures thereof; wherein M is hydrogen, one or more salt forming cations sufficient to satisfy charge balance, or mixtures thereof; y is an integer from 1 to about 22;
k) and mixtures thereof;
R$^3$ and R$^4$ are each independently methyl, ethyl, and mixtures thereof;
ii) optionally one or more fragrance raw materials;
iii) optionally fragrance carriers and other fragrance delivery adjuncts;
B) At least about 0.01% by weight, of a detersive surfactant selected from the group consisting of anionic, cationic, nonionic, zwitterionic, ampholytic surfactants, and mixtures thereof, and
C) the balance carriers and adjunct ingredients.

16. A composition according to claim 15 further comprising from about 1% to about 60% by weight, of a polyamine having the formula:

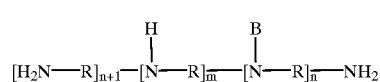

wherein R is $C_2$–$C_8$ alkylene, $C_3$–$C_8$ alkyl substituted alkylene, and mixtures thereof; B is a continuation of the backbone by branching and wherein the sum of n+m is 0 to 50.

17. A composition according to claim 16 comprising from about 0.01% to about 10% by weight, of a fragrance delivery system.

18. A composition according to claim 17 comprising from about 0.1% to about 1% by weight, of a fragrance delivery system.

19. A composition according to claim 16 comprising from about 0.1% to about 60% by weight, of a detersive surfactant.

20. A composition according to claim 19 comprising from about 0.1% to about 30% by weight, of a detersive surfactant.

21. A composition according to claim 16 wherein said surfactant is an anionic surfactant.

22. A composition according to claim 21 wherein R is ethylene, 1,2-propylene, 1,3-propylene.

23. A composition according to claim 22 wherein R is ethylene.

24. A composition according to claim 15 wherein $R^1$ and $R^2$ are each independently:
   a) $C_8$–$C_{12}$ linear or branched alkyl;
   b) $C_8$–$C_{12}$ linear or branched alkenyl;
   c) $C_2$–$C_{12}$ substituted or unsubstituted alkyleneoxy;
   d) $C_3$–$C_{12}$ substituted or unsubstituted alkyleneoxyalkyl;
   e) $C_7$–$C_{12}$ substituted or unsubstituted alkylenearyl;
   f) $C_6$–$C_{12}$ substituted or unsubstituted aryloxy;
   g) $C_8$–$C_{12}$ substituted or unsubstituted alkyleneoxyaryl;
   h) $C_7$–$C_{11}$ oxyalkylenearyl;
   i) $C_2$–$C_{12}$ alkylenecarboxy having the formula:

$$—(CH_2)_x R^9$$

wherein $R^9$ is —CHO, —$CO_2$M; —$CO_2R^{10}$, —$CONH_2$, —$CONHR^{10}$, —$CONR^{10}R^{11}$, and mixtures thereof; wherein $R^{10}$ and $R^{11}$ are each independently methyl or ethyl; $C_1$–$C_{12}$ linear or branched alkyl, M is sodium or potassium, x is an integer from 1 to 19.

25. A composition according to claim 24 wherein $R^1$ and $R^2$ are each independently:
   a) $C_8$–$C_{12}$ linear or branched alkyl;
   b) $C_8$–$C_{12}$ linear or branched alkenyl;
   c) $C_2$–$C_6$ substituted or unsubstituted alkyleneoxy;
   d) $C_3$–$C_6$ substituted or unsubstituted alkyleneoxyalkyl;
   e) $C_7$ substituted or unsubstituted alkylenearyl;
   f) $C_6$ substituted or unsubstituted aryloxy;
   g) $C_8$ substituted or unsubstituted alkyleneoxyaryl;
   h) $C_7$ oxyalkylenearyl;
   i) $C_2$–$C_6$ alkylenecarboxy having the formula:

$$—(CH_2)_x R^9$$

wherein $R^9$ and x are the same as defined herein above.

26. A composition according to claim 15 wherein $R^3$ and $R^4$ are each methyl.

27. A composition according to claim 15 wherein said adjunct ingredients are selected from the group consisting of builders, optical brighteners, bleaches, bleach boosters, bleach catalysts, bleach activators, soil release polymers, dye transfer agents, dispersents, enzymes, suds suppressers, dyes, perfumes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof.

* * * * *